US008530159B2

(12) United States Patent
Croce

(10) Patent No.: US 8,530,159 B2
(45) Date of Patent: Sep. 10, 2013

(54) MIR-29-BASED METHODS FOR THE DIAGNOSIS AND PROGNOSIS OF ACUTE MYELOID LEUKEMIA (AML)

(75) Inventor: Carlo M. Croce, Columbus, OH (US)

(73) Assignee: The Ohio State University Research Foundation, Columbus, OH (US)

(*) Notice: Subject to any disclaimer, the term of this patent is extended or adjusted under 35 U.S.C. 154(b) by 0 days.

(21) Appl. No.: 13/269,404

(22) Filed: Oct. 7, 2011

(65) Prior Publication Data

US 2012/0028831 A1 Feb. 2, 2012

Related U.S. Application Data

(62) Division of application No. 12/523,915, filed as application No. PCT/US2008/001157 on Jan. 29, 2008, now Pat. No. 8,034,560.

(60) Provisional application No. 60/898,578, filed on Jan. 31, 2007.

(51) Int. Cl.
*C12Q 1/68* (2006.01)

(52) U.S. Cl.
USPC ........................................................ 435/6.1

(58) Field of Classification Search
USPC ........................................................ 435/6.1
See application file for complete search history.

(56) References Cited

U.S. PATENT DOCUMENTS

| | | | |
|---|---|---|---|
| 6,187,536 B1 | 2/2001 | Weinberg et al. | |
| 7,888,010 B2 | 2/2011 | Brown et al. | |
| 7,919,245 B2 | 4/2011 | Brown et al. | |
| 2002/0132290 A1 | 9/2002 | Frazer | |
| 2005/0075492 A1 | 4/2005 | Chen et al. | |
| 2005/0164252 A1 | 7/2005 | Yeung | |
| 2007/0036765 A1 | 2/2007 | Civin et al. | |
| 2007/0259352 A1 | 11/2007 | Bentwich et al. | |
| 2009/0092974 A1* | 4/2009 | Davison et al. | 435/6 |
| 2009/0131356 A1 | 5/2009 | Bader et al. | |
| 2009/0233297 A1 | 9/2009 | Mambo et al. | |
| 2010/0099200 A1 | 4/2010 | Nazabal et al. | |
| 2010/0104662 A1 | 4/2010 | Oren et al. | |
| 2010/0196426 A1 | 8/2010 | Skog et al. | |
| 2010/0317610 A1 | 12/2010 | Croce | |

FOREIGN PATENT DOCUMENTS

| | | |
|---|---|---|
| CA | 2533701 A1 | 2/2005 |
| CA | 2587189 A1 | 12/2006 |
| FR | 2877350 A1 | 5/2006 |
| WO | 0076524 A1 | 12/2000 |
| WO | 2005013901 A3 | 2/2005 |
| WO | 2005060661 A2 | 7/2005 |
| WO | 2005079397 A2 | 9/2005 |
| WO | 2005103298 A2 | 11/2005 |
| WO | 2006108718 A1 | 10/2006 |
| WO | 2007016548 A2 | 2/2007 |
| WO | 2007112097 A2 | 10/2007 |
| WO | 2007112754 A2 | 10/2007 |
| WO | 2008/036168 A2 | 3/2008 |
| WO | 2008073915 A2 | 6/2008 |

OTHER PUBLICATIONS

Volinia et al. (PNAS 2006, 103:2257-2261).*
Garzon et al. Blood vol. 108, No. 11, part 1, pp. 49A, abstract#151, 48th Annual meeting of the American Society of Hematology Dec. 9-12, 2006.*
Giles et al. Blood 43rd Annual Meeting of the American Society of Hematology, Part 1; Orlando, FL, USA, Dec. 7-11, 2001, pp. 1-2.*
Australian Office Action, Application No. 2006291165 dated Feb. 13, 2012.
Australian Office Action, Application No. 2007227423 dated Apr. 13, 2012.
Australian Office Action, Application No. 2007205257 dated Dec. 22, 2011.
Australian Office Action, Application No. 2007205234 dated Sep. 20, 2011.
Australian Office Action, Application No. 2006291165 dated Aug. 23, 2011.
Canadian Intellectual Property Office, Requisition by the Examiner, Application No. 2,635,616, Dated Feb. 21, 2011.
Canadian Office Action, Application No. 2,635,616, dated Feb. 27, 20112.
Canadian Office Action, Application No. 2,617,581, dated Feb. 1, 2011.
Canadian Office Action, Application No. 2,617,581, dated Apr. 2, 2012.
Canadian Office Action, Application No. 2,621,441, dated Feb. 1, 2011.
Chinese Office Action, Application No. 200680036598.3 dated Feb. 24, 2011.
Chinese Office Action, Application No. 200780005821.2 dated Jan. 26, 2011.
Chinese Office Action, Application No. 20088011920639 dated May 3, 2012.
Chinese Office Action, Application No. 200780040146.7 dated May 25, 2011.
Chinese Office Action, Application No. 200680039776.8 dated Jun. 30, 2011.
Communication Concerning Office Action Received from Japanese Patent Office dated Jan. 30, 2012, Japanese Patent Application No. 2008-531200.
EP Search Report, Application No. 08782609.5 dated Oct. 28, 2010.
EP Search Report, Application No. 11196256.9 dated Feb. 28, 2012.
EP Search Report, Application No. 11196250.2 dated Apr. 24, 2012.
EP Search Report, Application No. 11196261.9 dated Feb. 28, 2012.
EP Search Report, Application No. 11196190.0 dated Apr. 24, 2012.
EP Search Report, Application No. 11196253.6 dated Apr. 24, 2012.
EP Search Report, Application No. 11196254.4 dated Feb. 28, 2012.
EP Search Report, Application No. 11196265.0 dated Mar. 5, 2012.
EP Search Report, Application No. 11196264-3 dated Feb. 28, 2012.
EP Search Report, Application No. 11196262.7 dated Feb. 28, 2012.
European Communication Pursuant to Article 94(3) EPC, Application No. 07717903.4, dated Apr. 25, 2012.
European Communication Pursuant to Article 94(3) EPC, Application No. 07867402.5, dated Apr. 10, 2012.

(Continued)

*Primary Examiner* — Brian Whiteman
(74) *Attorney, Agent, or Firm* — MacMillan, Sobanski & Todd, LLC

(57) ABSTRACT

The present invention provides novel methods and compositions for the diagnosis, prognosis and treatment of acute myeloid leukemia (AML). The invention also provides methods of identifying anti-AML agents.

17 Claims, 25 Drawing Sheets

(56) References Cited

OTHER PUBLICATIONS

European Communication Pursuant to Article 94(3) EPC, Application No. 06800599.0 dated Nov. 25, 2011.
European Communication Pursuant to Article 94(3) EPC, Application No. 08767439.6, dated Feb. 12, 2011.
European Communication Pursuant to Article 94(3) EPC, Application No. 07810382.7, dated Dec. 8, 2010.
European Communication Pursuant to Article 94(3) EPC, Application No. 07716208.9, dated Sep. 13, 2011.
European Communication Pursuant to Article 94(3) EPC, Application No. 07867402.5, dated Jan. 5, 2011.
European Communication Pursuant to Article 94(3) EPC, Application No. 08799295.4, dated Nov. 18, 2011.
European Communication Pursuant to Article 94(3)EPC, Application No. 06814375.9 dated Oct. 14, 2011.
European Communication Pursuant to Article 94(3) EPC, Application No. 08768266.2, dated Apr. 18, 2011.
European Communication Pursuant to Article 94(3) EPC, Application No. 08767439.9, dated Mar. 15, 2011.
European Seach Report, Application No. 09714868.8 dated Aug. 1, 2011.
European Seach Report, Application No. 11151749.6, dated Feb. 8, 2011.
European Search Reoprt, Application No. 08841700.1, dated Jan. 4, 2011.
European Search Report, Application No. 08770974.4, dated Oct. 21, 2011.
European Search Report, Application No. 11151772-8, dated Feb. 8, 2011.
European Search Report, Application No. 08798444.9-2402, PCT/US2008/073964, dated Dec. 16, 2010.
European Search Report, Application No. 09713926.5 dated Jul. 21, 2011.
European Search Report, Application No. 11151769-4, dated Feb. 8, 2011.
European Search Report, Application No. 08799295.4-2402, PCT/US2008/075565, dated Nov. 9, 2010.
European Search Report, Application No. 11151771-0, dated Feb. 8, 2011.
European Search Report, Application No. 08713330.2, dated Jul. 22, 2011.
European Supplementary Search Report, Application No. 09715064.3 dated May 24, 2011.
Japanese Office Action dated Feb. 24, 2012, Japanese Patent Application No. 2008-549532.
Japanese Office Action dated Feb. 24, 2012, Japanese Patent Application No. 2008-549555.
Japanese Office Action dated Jan. 4, 2012, Japanese Patent Application No. 2008-5251070.
Japanese Office Action dated Feb. 22, 2012, Japanese Patent Application No. 2008-549549.
PCT International Preliminary Report on Patentability, PCT/US2010/025173 filed Feb. 24, 2010, dated Sep. 9, 2011.
PCT International Preliminary Report on Patentability, PCT/US2009/065072 filed Nov. 19, 2009, dated Jun. 3, 2011.
PCT International Preliminary Report on Patentability, PCT/US2009/038214 filed Mar. 25, 2009.
PCT International Search Report and the Written Opinion, PCT/US2012/020911 filed Jan. 11, 2012, dated Apr. 25, 2012.
PCT Invitation to Pay Additional Fees, PCT/US2012/028016 filed Mar. 7, 2012, dated May 29, 2012.
Aiba, M. "Pathology of the Breast Carcinoma from the Viewpoint of the Proliferative Activity and Grade of Malignancy," JP J Cancer Clin, 2000, pp. 475-181, vol. 46, No. 5.
Alvarez-Secord, A. et al., "Maspin Expression in Epithelial Ovarian Cancer and Associations with Poor Prognosis: A Gynecologic Oncology Group Study," Gynecologic Oncology, 2006, pp. 390-397, vol. 101.
Ambros, V. et al., "A Uniform System for MicroRNA Annotation," RNA, 2003, pp. 277-279, vol. 9.
Baira, E. et al., "Ultraconserved Elements: Genomics, Function and Disease," RNA Biology, Jul. 2008, pp. 132-134, vol. 5, No. 3.
Bloomston, M. et al., "MicroRNA Expression Patterns to Differentiate Pancreatic Adenocarcinoma from Normal Pancreas and Chronic Pancreatitis," JAMA, May 2007, pp. 1901-1908 vol. 297, No. 1.
Blum, W. et al., "Clinical Response and miR-29b Predictive Significance in Older AML Patients Treated With a 10-Day Schedule of Decitabine," PNAS, Apr. 2010, pp. 7473-7478, vol. 107, No. 16.
Boland, C.R. et al., "Lynch Syndrome: Form, Function, Proteins, and Basketball," Gastroenterology, Aug. 2005, pp. 751-755, vol. 129, No. 2.
Braun et al., "p53-Responsive MicroRNAs 192 and 215 are Capable of Inducing Cell Cycle Arrest," Cancer Research, 2008, pp. 10094-10104, vol. 68.
Caldas, C. et al., "Sizing Up miRNAs as Cancer Genes," Nature Medicine, Jul. 2005, pp. 712-714, vol. 11, No. 7.
Cannistra, S.A., "Cancer of the Ovary," The New England Journal of Medicine, 2004 pp. 2519-2529, vol. 351, No. 25.
Castoldi, M. et al., "A Sensitive Array for MicroRNA Expression Profiling (miChip) Based on Locked Nucleic Acids (LNA)," RNA, 2006, pp. 913-920, vol. 12.
Chim, S.S.C. et al., "Detection and Characterization of Placental MicroRNAs in Maternal Plasma," Clinical Chemistry, 2008, pp. 482-490, vol. 54, No. 3.
Cui, S. et al., "MicroRNAs that Underlie Ovarian Cancer Development and Response to Chemotherapy," 98th AACR Annual Meeting, Apr. 14-18, 2007, Los Angeles, CA.
Davies, B.R. et al., "AZD6244 (ARRY-142886), a Potent Inhibitor of Mitogen-Activated Protein Kinase/Extracellular Signal-Regulated Kinase Kinase 1/2 Kinases: Mechanism of Action in vivo, Pharmacokinetic/Pharmacodynamic Relationship, and Potential for Combination in Preclinical Needs," Mol. Cancer Ther., Aug. 2007, vol. 6, No. 8, pp. 2209-2219.
Debernardi, S. et al., "MicroRNA miR-181a Correlates with Morphological Sub-Class of Acute Myeloid Leukemia and the Expression of its Target Genes in Global Genome-Wide Analysis," Leukemia, 2007, pp. 912-916, vol. 21.
Esquela-Kerscher, A. et al., "Oncomirs—MicroRNAs with a Role in Cancer," Nature Reviews:Cancer, Apr. 2006, pp. 259-269, vol. 6.
Felli, N. et al., "MicroRNAs 221 and 222 Inhibit Normal Erythropoiesis and Erythroleukemic Cell Growth via Kit Receptor Down-Modulation," PNAS, Dec. 2005, pp. 18081-18086, vol. 102, No. 50.
Feng, G. et al., "Elevated Serum-Circulating RNA in Patients with Conventional Renal Cell Cancer," Anticancer Research, 2008, pp. 321-326, vol. 28.
Flavin, RJ et al., "MicroRNA Gene Expression Profiling in Human Ovarian and Primary Peritoneal Serous Carcinomas" USCAP 96th Annual Meeting, Abstract #897, San Diego, CA, Mar. 2007.
Ford, L.P., "A MicroRNA Expression Signature of Human Solid Tumors Defines Cancer Gene Targets," Leukemia Research, 2006, pp. 511-513, vol. 30.
Fujuta, S. et al., "miR-21 Gene Expression Triggered by AP-1 is Sustained Through a Double-Negative Feedback Mechanism," J. Mol. Biol., Abstract, 2008, pp. 492-504, vol. 378.
Gang, M. et al., "Expression of Programmed Cell Death 4 and Its Clinicopathological Significance in Human Pancreatic Cancer," Abstract, 2005, pp. 597-600, vol. 27.
Garofalo, M. et al., "miR-221&222 Regulate TRAIL Resistance and Enhance Tumorigenicity through PTEN and TIMP3 Downregulation," Cancer Cell, Dec. 2009, pp. 498-509, vol. 16.
Garzon, R. et al., "MicroRNA Expression and Function in Cancer," TRENDS in Molecular Medicine, Oct. 2006, pp. 580-587, vol. 12, No. 12.
Garzon, R. et al., "MicroRNA Signatures Associated with Cytogenetics and Outcome in Acute Myeloid Leukemia," ASH Annual Meeting Abstracts, Nov. 2006, Abstract #151, Part 1, p. 498, vol. 108, Issue 11.
Griffths-Jones, S. et al., "miRBase: Tools for MicroRNA Genomics," Nucleic Acids Research, 2008, pp. D154-D157, vol. 36.
Griffths-Jones, S., "The MicroRNA Registry," Nucleic Acids Research, 2004, pp. D109-D111, vol. 32.
He, L. et al., "A MicroRNA Polycistron as a Potential Human Oncogene," Nature, Jun. 2005, pp. 828-833, vol. 435.

He, X. et al., "MicroRNA and Esophageal Carcinoma," Journal of Nanjing Medical University, 2007, pp. 201-206, vol. 21, No. 4.

Ishii, H. et al., "Effect of Adenoviral Transduction of the Fragile Histidine Triad Gene into Esophageal Cancer Cells," Cancer Research, Feb. 2001, pp. 1578-1584, vol. 61.

Jacobs, I.J. et al., "Prevalence Screening for Ovarian Cancer in Postmenopausal Women by CA 125 Measurement and Ultrasonography," BMJ, Apr. 1993, pp. 1030-1034, vol. 306.

Jacobs, I.J. et al., "Progress and Challenges in Screening for Early Detection of Ovarian Cancer," Molecular & Cellular Proteomics, 2004, pp. 355-366, vol. 3.

Jazbutyte, V. et al., "MicroNRA-21: From Cancer to Cardiovascular Disease," Current Drug Targets, Abstract, 2010, pp. 926-935, vol. 11.

Jemal, A. et al., "Cancer Statistics, 2008," CA Cancer J. Clin., 2008, pp. 71-96, vol. 58, No. 2.

Kelly, L.M. et al., "CT53518, A Novel Selective FLT3 Antagonist for the Treatment of Acute Myelogenous Leukemia (AML)," Cancer Cell, Jun. 2002, pp. 421-432, vol. 1.

Kozomara, A. et al., "miRBase: Integrating MicroRNA Annotation and Deep-Sequencing Data," Nucleic Acids Research, 2011, pp. D152-D157, vol. 39.

Lagos-Quintana, M. et al., "Identification of Tissue-Specific MicroRNAs from Mouse," Current Biology, Apr. 2002, pp. 735-739, vol. 12.

Landgraf, P. et al., "A Mammalian MicroRNA Expression Atlas Based on Small RNA Library Sequencing," Cell, Jun. 2007, pp. 1401-1414, vol. 129.

Lanza, G. et al., "mRNA/microRNA Gene Expression Profile in Microsatellite Unstable Colorectal Cancer," Molecular Cancer, 2007, pp. 1-11, vol. 6, No. 54.

Lawrie, C.H. et al., "Detection of Elevated Levels of Tumour-Associated MicroRNAs in Serum of Patients with Diffuse Large B-Cell Lymphoma," British Journal of Haematology, 2008, pp. 672-675, vol. 141.

Li, S.-C. et al., "Bioinformatic Discovery of MicroRNA Precursors from Human ESTs and Introns," BMC Genomics, 2006, vol. 7.

Li, Z. et al., "Inhibition of PRL-3 Gene Expression in Gastric Cancer Cell Line SGC7901 via MicroRNA Suppressed Reduces Peritoneal Metastasis," Biochemical and Biophysical Research, Sep. 2006, pp. 229-237, vol. 348, No. 1.

Lujambio, A. et al., "A MicroRNA DNA Methylation Signature for Human Cancer Metastasis," PNAS, Sep. 2008, pp. 13556-13561, vol. 105, No. 36.

Medina, P.P. et al., "OncomiR Addiction in an In Vivo Model of MicroRNA-21-Induced Pre-B-Cell Lymphoma," Nature Letters, Sep. 2010, pp. 86-91, vol. 467.

Medina, P.P., "OncomiR Addicton in an in vivo Model of MicroRNA-21-Induced Pre-B-Cell Lymphoma," Supplementary Information, Sep. 2010, p. 1-22.

Mendell, J.T., "miRiad Roles for the miR-17-92 Cluster in Development and Disease," Cell, 2008, pp. 217-.

Meng, F. et al., "MicroRNA-21 Regulates Expression of the PTEN Tumor Suppressor Gene in Human Hepatocellular Cancer," Gastroenterology, 2007, pp. 647-658, vol. 133.

Naegeli, K. et al., "Novel Mechanisms of Ovarian Cancer Growth Inhibition, via MicroRNA Downregulation and Oxidative Damage, by a Ratioanlly Designed Histone Deacetylase Inhibitor," Abstract #2475, 98th ACCR Annual Meeting, Apr. 14-18, 2007, Los Angeles, CA.

Nakajima, G. et al., "Non-Coding MicroRNAs HAS-LET-7G and HAS-MIR-181b are Associated with Chemoresponse to S-1 in Colon Cancer," Cancer Genomics & Proteomics, Sep. 2006, pp. 317-324, vol. 3, No. 5.

Nam, E.J. et al., "MicroRNA Expression Profiles in Serous Ovarian Carcinoma," Clinical Cancer Research, 2008, pp. 2690-2695, vol. 14, No. 9.

Nicoloso, M.S. et al., "MicroRNAs—The Micro Steering Wheel of Tumour Metastases," Nature Reviews: Cancer, Apr. 2009, pp. 293-302, vol. 9.

Nurden, A.T., "Qualitative Disorders of Platelets and Megakaryocytes," Journal of Thrombosis and Haemostasis, 2005, vol. 3, pp. 1773-1782.

Okada, H. et al., "MicroRNAs in Immune Regulation—Opportunities for Cancer Immunotherapy," The International Journal of Biochemistry & Cell Biology, 2010, pp. 1256-1261, vol. 42.

Olivier, R.I. et al., "CA125 and Transvaginal Ultrasound Monitoring in High-Risk Women Cannot Prevent the Diagnosis of Advanced Ovarian Cancer," Gynecologic Oncology, 2006, pp. 20-26, vol. 100.

Petrocca, F. et al., "MicroRNAs Deregulation in Gastric Cancer," PNAS, Apr. 2006, p. 1338, vol. 47, Abstract # 5690.

Pichiorri et al., "Downregulation of p53-Inducible MicroRNAs 192, 194 and 215 Impairs the p53/MDM2 Autoregulatory Loop in Multiple Myeloma Development," Cancer Cell, 2010, pp. 367-381, vol. 18.

Pichiorri, F. et al., "MicroRNAs Regulate Critical Genes Associated with Multiple Myeloma Pathogenesis," PNAS, Sep. 2008, pp. 12885-12890, vol. 105, No. 35.

Pineau, P. et al., "miR-221 Overexpression Contributes to Liver Tumorigenesis," PNAS, Jan. 2010, pp. 264-269, vol. 107, No. 1.

Porkka, K.P. et al., "MicroRNA Expression Profiling in Prostate Cancer," Cancer Research, 2007, pp. 6130-6135, vol. 67, No. 13.

Pruitt, K.D. et al., "NCBI Reference Sequence (RefSeq): A Curated Non-Redundant Sequence Database of Genomes, Transcripts and Proteins," Nucleic Acids Research, 2005, pp. D501-D504, vol. 33.

Ribas, J. et al., "The Transcriptional Regulation of miR-21, Its Multiple Transcripts, and Their Implication in Prostate Cancer," Cell Cycle, 2010, pp. 923-929, vol. 9.

Rossi, S. et al., "MicroRNA Fingerprinting of CLL Patients with Chromosome 17p Deletion Identify a miR-21 Score that Stratifies Early Survival," Blood, Aug. 2010, pp. 945-952, vol. 116, No. 6.

Ryu, J.K. et al., "Aberrant MicroRNA-155 Expression is an Early Event in the Multistep Progression of Pancreatic Adenocarcinoma," Pancreatology, 2010, pp. 66-73, vol. 10.

Saini, H. K. et al., "Annotation of Mammalian Primary MicroRNAs," BMC Genomics, 2008, vol. 9.

Saito, Y. et al., "Specific Activation of MicroRNA-127 with Downregulation of the Proto-Oncogene BCL6 by Chromatin-Modifying Drugs in Human Cancer Cells," Cancer Cell, Jun. 2006, pp. 435-443, vol. 9.

Santanam, U. et al., "Chronic Lymphocytic Leukemia Modeled in Mouse by Targeted miR-29 Expression," PNAS, Jul. 2010, pp. 12210-12215, vol. 107, No. 27.

Sasaki, Y.T.F. et al., "Coordinated Expression of ncRNAs and HOX mRNAs in the Human HOXA Locus," Biochemical and Biophysical Communications, 2007, pp. 724-730, vol. 357.

Schagen, F. et al., "Genetic Targeting of Adenovirus Vectors Using a Reovirus Sigmal-Based Attachment Protein," Molecular Therapy, May 2006, pp. 997-1005, vol. 13, No. 5.

Schetter, A.J. et al., "Association of Inflammation-Related and MicroRNA Gene Expression with Cancer Specific Mortality of Colon Adenocarcinoma," Clin. Cancer Res., Sep. 2009, pp. 5878-5887, vol. 15, No. 18.

Slack, F.J., "Big Roles for Small RNAs," Nature, Feb. 2010, p. 616, vol. 463.

Stamatopoulos, B. et al., "MicroRNA-29c and MicroRNA-233 Down-Regulation has In Vivo Significance in Chronic Lymphocytic Leukemia and Improves Disease Risk Stratification," Blood, May 2009, pp. 5237-5245, vol. 113, No. 21.

Suarez-Saiz, F.J. et al., "MicroRNA Expression Profiling in Acute Myelogenous Leukemia," Canada Blood, Nov. 2004, Abstract #1131, p. 320A.

Taccioli, C. et al., "Ucbase & miRfunc: A Database of Ultraconserved Sequences and MicroRNA Function," Nucleic Acids Research, 2009, pp. D41-D48, vol. 37.

Taylor, D.D. et al., "MicroRNA Signatures of Tumor-Derived Exosomes as Diagnostic Biomarkers of Ovarian Cancer," Gynecologic Oncology, 2008, pp. 13-21, vol. 110.

Thomson, M., Supplementary data for "A Custon Microarray Platform for Analysis of MicroRNA Gene Expression," Nature Methods, Oct. 2004, pp. 47-53, vol. 1, No. 1.

Tili, E. et al., "Expression and Function of Micro RNAs in Immune Cells During Normal or Disease State," International Journal of Medicine Sciences, 2008, pp. 73-79, vol. 5, No. 2.

Uil, T.G. et al., "Generation of an Adenoviral Vector Containing an Addition of a Heterologous Ligand to the Serotpe 3 Fiber Knob," Cancer Gene Therapy, Feb. 2003, pp. 121-124, vol. 10, No. 2.

Valeri, N. et al., "Modulation of Mismatch Repair and Genomic Stability by miR-155," PNAS, Apr. 2010, pp. 6982-6987, vol. 107, No. 15.

Vassilev et al., "In Vivo Activation of the p53 Pathway by Small-Molecule Antagonists of MDM2," Science, 2004, pp. 844-848, vol. 303.

Verschuur, A.C., "Acute Megakaryoblastic Leukemia," May 2004, pp. 1-5, Retrieved from the Internet: URL: http://www.orpga.net/data/patho/GB/uk-AMLM7.pdf.

Watson, D.I. et al., "MicroRNA Expression Profiles in Barrett's Oesophagus," RACS Annual Scientific Congress, 2007, pp. A45, vol. 77.

Wiemer et al., "The Role of MicroRNAs in Cancer: No Small Matter," European Journal of Cancer, Jun. 12, 2007, vol. 43, No. 10, pp. 1529-1544.

Wijermans, P.W., "Low Dose Azanucleosidesfor High Risk (s) MDS and AML," Haematologica Reports,Nov. 2006, pp. 74-76. vol. 2, Issue, 15.

Xi, Y. et al., "Prognostic Values of MicroRNAs in Colorectal Cancer," Biomarker Insights, Jan. 2006, pp. 113-121, vol. 1.

Zawacka-Pankau, J. et al., "Expression and Simple, One-Step Purification of Fragile Histidine Triad (FHIT) Tumor Suppressor Mutant Forms in *Escherichia coli* and their Interaction with Protoporphyrin IX," Biotechnology Letters, Jun. 2007, pp. 877-883, vol. 29, No. 6.

Zhao et al., "p53 Mediates the Negative Regulation of MDM2 by Orphan Receptor TR3," The EMBO Journal, 2006, pp. 5703-5715, vol. 25.

* cited by examiner

| Characteristic | 122 AML patients<br>Value | Validation set<br>(36) patients<br>Value |
|---|---|---|
| Age | | |
| Median | 60.3 | 55.17 |
| Range | (18-86) | (20-78) |
| Sex - no. (%) | | |
| Female | 47(38) | 19(53) |
| Male | 75(62) | 17(47) |
| White cell count x$10^9$ /L | | |
| Median | 46.83 | 68.1 |
| Range | (0.7-278) | (1.2-147) |
| Bone marrow blasts count % | | |
| Median | 62 | 69 |
| Range | 20-99 | (20-98) |
| FAB | | |
| M0 | 7 (5) | 2 (5.5) |
| M1 | 12 (10) | 5 (14) |
| M2 | 22 (18) | 11(30.5) |
| M3 | 4 (3) | 0 |
| M4 | 38 (31) | 7(19) |
| M5 | 15 (12) | 3 (8.4) |
| M6 | 11 (9) | 1(2.8) |

Figure 4 - Table 1

| | | |
|---|---|---|
| M7 | 5 (4) | 1(2.8) |
| Not determined* | 8 (6) | 6 (17) |
| Cytogenetics † | | |
| t(15;17) (q22;q21) | 4 (3.4) | 0 |
| inv(16)/ t(16;16) | 4 (34) | 0 |
| Normal Karyotype | 45 (39) | 12 (33.7) |
| 11q23 rearrangements | 9 (7.8) | 3 (8.4) |
| -7 | 4 (3.4) | 0 |
| -5 | 1 (0.8) | 0 |
| del 5(q) | 3 (2.6) | 1(2.8) |
| del 9(q) | 2 (1.7) | 1(2.8) |
| del 13 (q12;q22) | 2 (1.7) | 0 |
| +8 | 5 (4.4) | 1 (2.8) |
| +4 | 2 (1.7) | 0 |
| Complex karyotype‡ | 25 (21.5) | 11 (30.5) |
| Other abnormal karyotypes | 10 (8.6) | 7 (19) |
| Vital status –no/ (%) | | |
| Dead | 81 (66) | 28 (77) |
| Alive | 41 (33) | 8 (23) |

Figure 4 continued - Table 1

| MicroRNA | Group Signature | Location | Putative targets |
|---|---|---|---|
| *miR-181a,b* | Up in AML M0-M1 | 9q33 | *RUNX1,KIT* |
| *miR-146* | Up in AML M0-M1 | 5q33 | *KIT, SDFR1* |
| *miR-145* | Up in AML M6-M7, Down in M4-M5 | 5q32 | *FLI1, CBFB* |
| *miR-126* | Up in AML M6-M7 and complex karyotype Down in normal karyotype and M4-M5 | 9q34 | *Crk, HOXA9* |
| *miR-135b* | Down in t(15;17) | 1q32 | *LTZS1,AKT3* |
| *miR-10a* | Up in normal karyotype | 17q21 | *HOXA1, VEGFR* |
| *miR-10b* | Up in normal karyotype | 2q31 | *HOXA1, VEGFR* |
| *miR-326* | Up in 11q23 rearrangements. | 11q13 | *CEBPA, RAP1B* |
| *miR-194* | Up in 11q23 rearrangements | 11q13 | *MEIS1, EIF2C1* |
| *miR-29b* | Down in 11q23 rearrangements | 7q32 | *MCL1, DNMT3B* |
| *miR-34b* | Down in 11q23, Up in normal karyotype | 11q23 | *NOTCH1, MYB* |
| *MiR-124a* | Up in +8 | 8p23 | *SP3, MITF* |
| *MiR-30d* | Up in +8 | 8q24 | *RARB,JUNB* |

Figure 5 - Table 2

| MicroRNA | Expression in patients with short survival | Genomic Location | Putative targets |
|---|---|---|---|
| *miR-25* | High | 7q22 | *JUN,GATA2* |
| *miR-20* | High | 13q31 | *E2F3, RUNX1* |
| *miR-17-5p* | High | 13q31 | *E2F3, RUNX1* |
| *miR-182* | High | 7q32 | *MITF, CEBPA* |
| *miR-199a* | High | 19q13 | *RUNX1, PAX3* |
| *miR-199b* | High | 9q34 | *RUNX1, PAX3* |
| *miR-191* | High | 3p21 | *CEBPB,MECP* |

Figure 6 - Table 3

| ID | Name |
|---|---|
| HSHELA01 | Human HeLa cell Jo-1 tRNA-His (GUG) |
| HSTRNL | Human transfer RNA-Leu (MAA) |
| HSU2SNRNA3P | H.sapiens U2 snRNA |
| HSU2SNRNA5P | H.sapiens U2 snRNA |
| HSU4SNRNA3P | H.sapiens U4 snRNA |
| HSU4SNRNA5P | H.sapiens U4 snRNA |
| HSU6SNRNA3P | H.sapiens U6 snRNA |
| HSU6SNRNA5P | H.sapiens U6 snRNA |
| Human GAPDH | H.sapiens GAPDH |
| HUMTRAB | Human Ala-tRNA |
| HUMTRF | Human Phe-tRNA |
| HUMTRMI No1 | Human initiator Met-tRNA-i |
| HUMTRMI No2 | Human initiator Met-tRNA-i |
| HUMTRMI3P | Human initiator Met-tRNA-i |
| HUMTRMI5P | Human initiator Met-tRNA-i |
| HUMTRN | Human Asn-tRNA |
| HUMTRS | Human transfer RNA-Ser |
| HUMTRV1A | Human Val-tRNA-1a |

Figure 7 - Table 4

| Down-regulated in AML | SAM Score[*] | Fold Change | FDR (%)[†] |
|---|---|---|---|
| hsa-mir-126 | -3.28 | 0.21 | 0 |
| hsa-mir-130a | -2.90 | 0.29 | 0 |
| hsa-mir-130b prec | -2.56 | 0.37 | 0 |
| hsa-mir-135 | -2.55 | 0.38 | 0 |
| hsa-mir-93 | -2.52 | 0.08 | 0 |
| hsa-mir-146 | -2.47 | 0.41 | 0 |
| hsa-mir-106b | -2.43 | 0.36 | 0 |
| hsa-mir-224 | -2.39 | 0.32 | 0 |
| hsa-mir-125a | -2.18 | 0.50 | 0 |
| hsa-mir-92 | -2.13 | 0.46 | 0 |
| hsa-mir-106a | -2.12 | 0.46 | 0 |
| hsa-mir-95 | -2.07 | 0.04 | 0 |
| hsa-mir-155 | -2.03 | 0.49 | 0 |
| hsa-mir-25 | -2.01 | 0.50 | 0 |
| hsa-mir-96 | -1.94 | 0.25 | 0 |
| hsa-mir-124a | -1.92 | 0.37 | 0 |
| hsa-mir-18 | -1.89 | 0.38 | 0 |
| hsa-mir-20 | -1.87 | 0.50 | 0 |
| hsa-let-7d | -1.80 | 0.48 | 0 |
| hsa-mir-26a | -1.76 | 0.48 | 0 |
| hsa-mir-128b-prec | -1.72 | 0.32 | 0 |
| hsa-mir-222 | -1.71 | 0.50 | 0 |
| hsa-mir-101 | -1.67 | 0.50 | 0 |
| hsa-mir-338 | -1.54 | 0.31 | 0 |
| hsa-mir-184-prec | -1.52 | 0.48 | 0 |
| hsa-mir-371 | -1.51 | 0.38 | 0 |
| hsa-mir-199b | -1.44 | 0.03 | 0 |
| hsa-mir-29b | -1.40 | 0.12 | 0 |
| hsa-mir-301 | -1.37 | 0.47 | 0 |

[*] SAM identifies genes with statistically significant changes in expression by assimilating a set of gene-specific scores (i.e. paired $t$ tests). Each gene is assigned a score on the basis of its change in gene expression relative to the standard deviation of repeated measurements for that gene. Genes with scores greater than a threshold are deemed potentially significant.

[†] The percentage of such genes identified by chance is the q-value o False Discovery Rate.

Figure 8 - Table 5

| MicroRNA | Sam Score | Fold Change | FDR (%) |
|---|---|---|---|
| * hsa-mir-181c | 2.58 | 2.78 | 0 |
| * hsa-mir-181a | 2.49 | 2.71 | 0 |
| hsa-mir-30b | 2.48 | 2.66 | 0 |
| * hsa-mir-192 | 2.46 | 4.89 | 0 |
| hsa-mir-130a | 2.45 | 2.53 | 0 |
| hsa-mir-30c | 2.44 | 2.71 | 0 |
| * hsa-mir-146 | 2.40 | 2.11 | 0 |
| hsa-mir-30c-prec | 2.31 | 2.67 | 0 |
| * hsa-mir-26a-prec | 2.26 | 2.15 | 0 |
| * hsa-mir-181b | 1.99 | 2.67 | 0 |
| * hsa-mir-124a | 1.99 | 2.16 | 0 |
| * hsa-mir-128b | 1.95 | 2.83 | 0 |

All miRNAs are up-regulated.
* MiRNAs found also up-regulated in treated AML patients with FAB M0-M1 vs. other FAB subtypes.

Figure 9 - Table 6

| MicroRNA | SAM Score | Fold Change | FDR (%) |
|---|---|---|---|
| hsa-mir-135b | -3.51 | 0.36 | 0 |
| hsa-mir-99b-prec | -2.25 | 0.35 | 0 |
| hsa-mir-132-prec | -2.19 | 0.28 | 0 |
| hsa-mir-95 | -1.93 | 0.07 | 0 |
| hsa-let-7d | -1.75 | 0.3 | 0 |

All miRNAs are down-regulated.

Figure 10 - Table 7

| miRNA | SAM Score | Fold Change | FDR (%) |
|---|---|---|---|
| *hsa-mir-21* | 2.53 | 2.52 | 0 |
| *hsa-miR-126* | -2.85 | 0.49 | 0 |
| *hsa-mir-331-prec* | -2.55 | 0.45 | 0 |
| *hsa-mir-145* | -2.37 | 0.38 | 0 |
| *hsa-mir-143* | -2.35 | 0.44 | 0 |
| *hsa-mir-193* | -2.33 | 0.37 | 0 |
| *hsa-mir-340* | -2.04 | 0.44 | 0 |
| *hsa-mir-204* | -1.90 | 0.43 | 0 |
| *hsa-mir-206* | -1.90 | 0.47 | 0 |
| *hsa-mir-29c* | -1.86 | 0.48 | 0 |
| *hsa-mir-188* | -1.81 | 0.50 | 0 |
| *hsa-mir-204-prec* | -1.76 | 0.37 | 0 |
| *hsa-mir-128a* | -1.75 | 0.48 | 2.5 |
| *hsa-mir-202* | -1.74 | 0.48 | 2.5 |
| *hsa-mir-194* | -1.72 | 0.45 | 2.5 |
| *hsa-mir-299* | -1.72 | 0.48 | 2.5 |
| *hsa-mir-126-prec* | -1.71 | 0.36 | 2.5 |
| *hsa-mir-190* | -1.71 | 0.45 | 2.5 |
| *hsa-mir-183-prec* | -1.54 | 0.45 | 2.5 |

MiRNAs in red are up-regulated, in green down-regulated.
All miRNAs except *miR-21* and *mR-331* were also found differentially expressed in treated AML patients with FAB M4-M5 compared with other FAB subtypes.

Figure 11 - Table 8

| miRNA | SAM Score | Fold Change | FDR (%) |
|---|---|---|---|
| * hsa-mir-126 | 4.61 | 4.42 | 0 |
| hsa-mir-204 | 4.58 | 3.51 | 0 |
| hsa-mir-190 | 4.27 | 3.51 | 0 |
| * hsa-mir-145 | 4.22 | 5.22 | 0 |
| hsa-mir-183-prec | 4.19 | 2.72 | 0 |
| hsa-mir-205 | 4.18 | 2.66 | 0 |
| hsa-mir-196b | 4.11 | 3.32 | 0 |
| hsa-mir-203-prec | 4.09 | 2.44 | 0 |
| hsa-mir-200c | 3.94 | 2.29 | 0 |
| hsa-mir-206 | 3.92 | 3.07 | 0 |
| hsa-mir-203 | 3.92 | 2.53 | 0 |
| * hsa-mir-125a-prec | 3.89 | 2.79 | 0 |
| hsa-mir-204-prec | 3.87 | 2.92 | 0 |
| hsa-mir-197 | 3.85 | 3.09 | 0 |
| hsa-mir-188 | 3.85 | 2.62 | 0 |
| * hsa-mir-143 | 3.75 | 3.16 | 0 |
| hsa-let-7a-2-prec | -3.95 | 0.12 | 0 |
| * hsa-mir-181b | -3.82 | 0.30 | 0 |
| * hsa-mir-26a | -3.77 | 0.02 | 0 |
| hsa-mir-30b | -3.54 | 0.32 | 0 |
| hsa-mir-181c | -3.37 | 0.27 | 0 |
| hsa-mir-181b | -3.01 | 0.28 | 0 |
| hsa-mir-30c-prec | -3.01 | 0.20 | 0 |
| hsa-mir-30c | -2.85 | 0.35 | 0 |
| * hsa-mir-34bNo2 | -2.83 | 0.03 | 0 |
| hsa-mir-23a | -2.79 | 0.50 | 0 |
| hsa-mir-324 | -2.60 | 0.27 | 0 |
| hsa-mir-21 | -2.60 | 0.22 | 0 |
| hsa-mir-181b-prec | -2.57 | 0.45 | 0 |
| hsa-mir-16-2 | -2.55 | 0.41 | 0 |

MiRNAs in red are up-regulated, in green down-regulated.
* These miRNAs were found also differentially expressed in treated AML patients (4) with FAB M6-M7 subtype compared with all the other FAB subtypes (48).

Figure 12 - Table 9

| miRNA correlated with high WBC | SAM Score | FDR (%) |
|---|---|---|
| hsa-mir-155 | 2.96 | 0 |
| hsa-mir-30e | 2.79 | 0 |
| hsa-mir-23b | 2.73 | 0 |
| hsa-mir-181b | 2.59 | 0 |
| hsa-mir-213 | 2.59 | 0 |
| hsa-mir-221 | 2.58 | 0 |
| hsa-mir-29b | 2.58 | 0 |
| hsa-mir-95 | 2.56 | 0 |
| hsa-mir-128b | 2.54 | 0 |
| hsa-mir-27a | 2.52 | 0 |
| hsa-mir-181c | 2.52 | 0 |
| hsa-mir-92 | 2.45 | 0 |
| hsa-mir-181a | 2.44 | 0 |
| hsa-mir-23a | 2.43 | 0 |
| hsa-mir-214 | 2.42 | 0 |
| hsa-mir-30b | 2.39 | 0 |
| hsa-mir-30c | 2.36 | 0 |
| hsa-mir-26b | 2.35 | 0 |
| hsa-mir-21 | 2.33 | 0 |
| hsa-mir-222 | 2.32 | 0 |
| miRNAs correlated with high BM blasts % | | |
| hsa-mir-30b | 4.54 | 0 |
| hsa-mir-30c | 4.31 | 0 |
| hsa-mir-192 | 3.95 | 0 |
| hsa-mir-181a | 3.90 | 0 |
| hsa-mir-155 | 3.82 | 0 |
| hsa-let-7a-2 | 3.73 | 0 |
| hsa-mir-181b | 3.69 | 0 |
| hsa-mir-181b-prec | 3.65 | 0 |
| hsa-mir-34b | 3.65 | 0 |
| hsa-mir-181c | 3.64 | 0 |
| hsa-mir-219 | 3.55 | 0 |
| hsa-mir-214 | 3.51 | 0 |
| hsa-mir-213 | 3.49 | 0 |
| hsa-mir-301No2 | 3.38 | 0 |
| hsa-mir-26a | 3.37 | 0 |
| miRNAs correlated with high peripheral blasts % | | |
| hsa-mir-133b | 2.97 | 0 |
| hsa-mir-213 | 2.91 | 0 |
| hsa-mir-214 | 2.75 | 0 |
| hsa-mir-25 | 2.71 | 0 |
| hsa-mir-181a | 2.63 | 0 |
| hsa-mir-181b | 2.54 | 0 |

Figure 13 - Table 10

| | | |
|---|---|---|
| *hsa-mir-220* | 2.42 | 0 |
| *hsa-mir-92* | 2.39 | 0 |
| *hsa-mir-184* | 2.28 | 0 |
| *hsa-mir-92* | 2.26 | 0 |
| *hsa-mir-124a* | 2.22 | 0 |
| *hsa-mir-129-prec* | 2.22 | 0 |
| *hsa-mir-100* | 2.20 | 0 |
| *hsa-mir-181b* | 2.12 | 0 |
| *hsa-mir-135* | 2.01 | 0 |
| *hsa-mir-155* | 2.00 | 0 |
| *hsa-mir-222* | 1.93 | 0 |
| *hsa-mir-181c* | 1.85 | 0 |

All miRNAs are up-regulated (red) and have a positive correlation with WBC count, PB and BM blast percentage. These results were obtained by using quantitative SAM analysis. MiRNAs highlighted in yellow are shared in at least two signatures.

Figure 13 continued - Table 10

| MicroRNA | SAM Score | Fold Change | FDR (%) |
|---|---|---|---|
| hsa-mir-34b | 4.27 | 3.03 | 0 |
| hsa-mir-10a | 3.64 | 4.07 | 0 |
| hsa-mir-10b | 3.48 | 3.13 | 0 |
| hsa-mir-26a | 3.42 | 2.72 | 0 |
| hsa-mir-30c | 3.41 | 2.26 | 0 |
| hsa-let-7a-2 | 3.24 | 2.25 | 0 |
| hsa-mir-16-2 | 2.92 | 2.02 | 0 |
| hsa-mir-21 | 2.84 | 2.58 | 0 |
| hsa-mir-181b | 2.54 | 2.21 | 0 |
| hsa-mir-368 | 2.02 | 2.68 | 0 |
| hsa-mir-192 | 1.97 | 2.75 | 0 |
| hsa-mir-126 | -3.85 | 0.31 | 0 |
| hsa-mir-203 | -3.21 | 0.41 | 0 |
| hsa-mir-200c | -3.10 | 0.45 | 0 |
| hsa-mir-200c-prec | -3.03 | 0.39 | 0 |
| hsa-mir-203-prec | -3.00 | 0.43 | 0 |
| hsa-mir-182 | -3.00 | 0.38 | 0 |
| hsa-mir-198-prec | -2.98 | 0.36 | 0 |
| hsa-mir-204 | -2.98 | 0.41 | 0 |
| hsa-mir-205-prec | -2.97 | 0.5 | 0 |
| hsa-mir-183-prec | -2.96 | 0.42 | 0 |
| hsa-mir-196b | -2.94 | 0.42 | 0 |
| hsa-mir-193 | -2.80 | 0.42 | 0 |
| hsa-mir-182-prec | -2.78 | 0.38 | 0 |
| hsa-mir-191 | -2.76 | 0.43 | 0 |
| hsa-mir-199a | -2.70 | 0.42 | 0 |
| hsa-mir-194 | -2.61 | 0.36 | 0 |
| hsa-mir-204-prec | -2.60 | 0.24 | 0 |
| hsa-mir-183 | -2.56 | 0.28 | 0 |
| hsa-mir-299 | -2.55 | 0.43 | 0 |
| hsa-mir-193-prec | -2.43 | 0.45 | 0 |
| hsa-mir-30b-prec | -2.28 | 0.55 | 0 |

All miRNAs, except *miR-368* and *miR-192* were found also differentially expressed in treated AML patients with normal karyotype (10) compared with treated AML patients with abnormal karyotype (38).

MiRNAs in red are up-regulated, in green down-regulated.

Figure 14 - Table 11

| MicroRNA | SAM Score | Fold Change | FDR (%) |
|---|---|---|---|
| hsa-mir-326 | 3.74 | 5.49 | 0 |
| hsa-mir-219 | 2.42 | 2.60 | 6.2 |
| hsa-mir-194 | 2.24 | 2.73 | 6.2 |
| hsa-mir-301 | 2.19 | 2.65 | 6.2 |
| hsa-miR-324 | 2.05 | 2.33 | 6.9 |
| hsa-mir-339 | 2.04 | 2.51 | 6.9 |
| hsa-mir-99b | 1.86 | 2.03 | 7.3 |
| hsa-mir-328 | 1.80 | 2.31 | 7.6 |
| hsa-mir-34b | -5.46 | 0.12 | 0 |
| hsa-mir-15a | -4.13 | 0.11 | 0 |
| hsa-mir-29a | -4.00 | 0.10 | 0 |
| hsa-mir-29c | -3.98 | 0.02 | 0 |
| hsa-mir-372 | -3.68 | 0.15 | 0 |
| hsa-mir-30a | -3.62 | 0.18 | 0 |
| hsa-mir-29b | -3.60 | 0.02 | 0 |
| hsa-mir-30e | -3.58 | 0.13 | 0 |
| hsa-mir-196a | -3.57 | 0.39 | 0 |
| hsa-let-7f | -3.52 | 0.20 | 0 |
| hsa-mir-102 | -3.40 | 0.01 | 0 |
| hsa-mir-331 | -3.36 | 0.10 | 0 |
| hsa-mir-299 | -3.04 | 0.01 | 0 |
| hsa-mir-29a-prec | -3.00 | 0.16 | 0 |
| hsa-mir-193 | -2.86 | 0.04 | 0 |

MiRNAs in red are up-regulated, in green down-regulated.
The same signature was observed in an independent set of treated patients with 11q23 (4) vs. other cytogenetic abnormalities (44), except miR-372, miR-196a and miR-193.

Figure 15 - Table 12

| miRNA | SAM Score(d) | Fold Change | FDR (%) |
|---|---|---|---|
| * hsa-mir-126 | 3.03 | 2.71 | 0 |
| * hsa-mir-193 | 3.00 | 2.19 | 0 |
| * hsa-mir-204 | 2.96 | 2.39 | 0 |
| * hsa-mir-9-3 | 2.51 | 2.08 | 0 |
| hsa-mir-145 | 2.45 | 2.20 | 0 |
| * hsa-mir-128a-prec | 2.11 | 2.13 | 0 |
| hsa-mir-30c | -2.90 | 0.30 | 0 |
| * hsa-mir-301 | -2.83 | 0.32 | 0 |
| hsa-mir-30b | -2.62 | 0.35 | 0 |
| hsa-mir-30c-prec | -2.57 | 0.33 | 0 |
| hsa-mir-23a-prec | -2.50 | 0.46 | 0 |
| * hsa-mir-26a | -2.36 | 0.49 | 0 |
| hsa-mir-10a | -2.26 | 0.17 | 0 |
| * hsa-mir-26a-prec | -2.18 | 0.47 | 0 |
| hsa-mir-16-2 | -2.06 | 0.46 | 0 |
| hsa-mir-222-prec | -1.94 | 0.49 | 0 |
| hsa-mir-16-1 | -1.93 | 0.45 | 0 |
| hsa-mir-10b-prec | -1.87 | 0.28 | 0 |
| hsa-mir-30e | -1.84 | 0.48 | 0 |
| hsa-mir-21 | -1.77 | 0.49 | 0 |
| hsa-mir-155 | -1.62 | 0.49 | 0 |
| hsa-mir-181c | -1.61 | 0.46 | 0 |
| hsa-mir-10a-prec | -1.24 | 0.49 | 2.3 |
| hsa-mir-192 | -1.20 | 0.44 | 2.3 |

MiRNAs in red are up-regulated, in green down-regulated.
* These miRNAs were also found differentially expressed in treated patients with complex karyotype (14) vs. non complex, including normal karyotype (34).

Figure 16 - Table 13

| miRNA | SAM Score | Fold Change | FDR (%) |
|---|---|---|---|
| hsa-mir-204 | 2.27 | 2.15 | 0 |
| hsa-mir-126 | 2.26 | 4.03 | 0 |
| hsa-mir-205 | 2.19 | 2.05 | 0 |
| hsa-mir-190 | 2.14 | 2.46 | 0 |
| hsa-let-7d | 2.12 | 2.62 | 0 |
| hsa-mir-196a | 1.95 | 2.42 | 0 |
| hsa-mir-197 | 1.95 | 2.00 | 0 |
| hsa-mir-188 | 1.89 | 2.13 | 0 |
| hsa-mir-204-prec | 1.87 | 2.89 | 0 |
| hsa-mir-125a-prec | 1.86 | 2.38 | 0 |
| hsa-mir-18 | 1.64 | 6.05 | 2.53 |
| hsa-mir-186 | 1.55 | 2.74 | 4.21 |
| hsa-mir-196a prec | 1.54 | 2.05 | 4.21 |
| hsa-mir-9 | 1.49 | 2.02 | 4.21 |

All miRNAs are up-regulated.

Figure 17 - Table 14

| miRNA | SAM Score | Fold Change | FDR (%) |
|---|---|---|---|
| hsa-mir-337 | 3.49 | 29.94 | 0 |
| hsa-mir-192-prec | 3.41 | 13.49 | 0 |
| hsa-mir-337-prec | 3.25 | 14.05 | 0 |
| hsa-mir-184 | 3.21 | 25.49 | 0 |
| hsa-mir-302b | 3.06 | 4.93 | 0 |
| hsa-mir-206-prec | 2.95 | 13.16 | 0 |
| hsa-mir-105 | 2.94 | 11.05 | 0 |
| hsa-let-7d | 2.87 | 8.85 | 0 |
| hsa-mir-153 | 2.86 | 14.2 | 0 |
| * hsa-mir-124a | 2.78 | 10.67 | 0 |
| hsa-mir-215 | 2.69 | 13.19 | 0 |
| hsa-mir-1 | 2.68 | 199.7 | 0 |
| hsa-mir-194 | 2.62 | 18.13 | 0 |
| hsa-mir-199b-prec | 2.61 | 9.87 | 0 |
| hsa-mir-29c | 2.59 | 8.19 | 0 |

Figure 18 - Table 15

| | | | |
|---|---|---|---|
| *hsa-mir-208* | 2.56 | 11.65 | 0 |
| *hsa-mir-199a* | 2.54 | 14.01 | 0 |
| *hsa-mir-24-1* | 2.49 | 5.21 | 0 |
| *hsa-miR-302c* | 2.47 | 6.37 | 0 |
| *hsa-mir-338-prec* | 2.42 | 5.67 | 0 |
| *hsa-mir-367* | 2.41 | 9.11 | 0 |
| *hsa-mir-200a* | 2.41 | 4.19 | 0 |
| *hsa-mir-183* | 2.38 | 33.93 | 0 |
| *hsa-mir-199b* | 2.38 | 7.23 | 0 |
| *hsa-mir-372-prec* | 2.35 | 6.11 | 0 |
| *hsa-mir-143* | 2.35 | 5.56 | 0 |
| *hsa-mir-96* | 2.31 | 11.59 | 0 |
| *hsa-mir-204-prec* | 2.26 | 6.16 | 0 |
| *hsa-mir-29b* | 2.26 | 6.91 | 0 |
| *hsa-mir-202* | 2.25 | 5.64 | 0 |
| *hsa-mir-340* | 2.23 | 4.75 | 0 |
| *hsa-mir-102* | 2.17 | 8.11 | 0 |
| *hsa-mir-191* | 2.13 | 9.48 | 0 |
| *hsa-let-7i* | 2.11 | 6.78 | 0 |
| *hsa-mir-184-prec* | 2.11 | 5.69 | 0 |
| *hsa-miR-302b-prec* | 2.11 | 4.76 | 0 |
| *hsa-mir-30a* | 2.09 | 2.84 | 0 |
| *hsa-mir-9-3* | 2.08 | 4.11 | 0 |
| *hsa-mir-26a-prec* | 2.07 | 3.72 | 0 |
| *hsa-mir-124a-3* | 2.07 | 7.55 | 0 |
| *hsa-mir-203* | 2.03 | 6.99 | 0 |
| *hsa-mir-302a* | 2.02 | 11.36 | 0 |
| *hsa-mir-199a* | 2.01 | 8.93 | 0 |
| *hsa-mir-206* | 1.99 | 4.55 | 0 |
| *hsa-mir-197* | 1.98 | 5.25 | 0 |
| *hsa-mir-198* | 1.97 | 12.42 | 0 |
| *hsa-mir-372* | 1.95 | 4.99 | 0.68 |
| *hsa-mir-182* | 1.95 | 9.29 | 0.68 |
| *hsa-mir-129-prec* | 1.95 | 8.72 | 0.68 |
| *hsa-mir-193* | 1.92 | 8.72 | 0.68 |
| *hsa-mir-325* | 1.92 | 2.82 | 0.68 |
| *hsa-mir-183-prec* | 1.92 | 7.61 | 0.68 |
| *hsa-mir-196b-prec* | 1.92 | 4.89 | 0.68 |
| *hsa-mir-182-prec* | 1.92 | 8.62 | 0.68 |
| *hsa-mir-192* | 1.89 | 8.6 | 0.68 |
| *hsa-mir-367-prec* | 1.87 | 2.82 | 0.68 |

Figure 18 continued - Table 15

|  | miRNA | | | |
|---|---|---|---|---|
|  | hsa-mir-299-prec | 1.87 | 6.83 | 0.68 |
|  | hsa-mir-200c-prec | 1.85 | 6.65 | 0.68 |
|  | hsa-mir-204 | 1.84 | 5.11 | 0.68 |
|  | hsa-mir-299 | 1.84 | 3.37 | 0.68 |
|  | hsa-mir-29a | 1.83 | 2.29 | 1 |
|  | hsa-mir-203-prec | 1.77 | 6.73 | 1 |
|  | hsa-mir-331-prec | 1.76 | 3.81 | 1 |
|  | hsa-mir-95 | 1.75 | 3.52 | 1 |
| * | hsa-mir-30d-prec | 1.73 | 2.04 | 1 |
|  | hsa-mir-200c | 1.72 | 5.72 | 1 |
|  | hsa-mir-205 | 1.71 | 5.41 | 1 |
|  | hsa-mir-196a-prec | 1.67 | 3.76 | 1 |
|  | hsa-mir-17-prec | 1.66 | 1.97 | 1 |
|  | hsa-mir-103 | 1.65 | 2.56 | 1 |
|  | hsa-mir-193-prec | 1.63 | 4.16 | 1 |
|  | hsa-mir-93 | 1.61 | 2.66 | 1 |
|  | hsa-mir-373-prec | 1.57 | 2.92 | 1 |
|  | hsa-mir-190 | 1.54 | 5.38 | 1 |
|  | hsa-miR-373 | 1.53 | 3.24 | 1 |
|  | hsa-mir-196b-prec | 1.53 | 3.66 | 1 |
|  | hsa-mir-154 | 1.48 | 4.06 | 1.88 |
|  | hsa-mir-19b-1 | 1.47 | 2.48 | 1.88 |
|  | hsa-mir-196-1 | 1.46 | 2.88 | 1.88 |
|  | hsa-let-7i | 1.46 | 1.67 | 1.88 |
|  | hsa-mir-324 | 1.42 | 2.84 | 1.88 |
|  | hsa-mir-371-prec | 1.34 | 2.95 | 2.75 |

* These miRNAs are located at Chromosome 8.
For this analysis we included only samples with isolated trisomy 8. These samples were compared with other AML samples with known cytogenetics, excluding those samples with trisomy 8 as a secondary cytogenetics abnormality.
All miRNAs are up-regulated.

Figure 18 continued - Table 15

| Characteristic | Value |
| --- | --- |
| AGE | 52 |
| | (18-83) |
| Sex female | 25(46) |
| Male | 29(54) |
| White count x $10^9$ / L | |
| median | 50.3 |
| range | (2.4-335) |
| Bone marrow blasts % | 64.2 |
| | (20-99) |
| FAB no. (%) | |
| M0 | 1(1.8) |
| M1 | 10(18) |
| M2 | 15(28) |
| M4 | 8(15) |
| M5 | 2(3.7) |
| M6 | 3(5.5) |
| M7 | 2(3.7) |
| Unknown | 13(24) |
| Cytogenetics | |
| normal karyotype | 10(18) |
| -7 | 1(1.8) |
| 11q23 rearrangements | 4(7) |
| t (6;9)(p23;q34) | 2(3.7) |
| +8 | 5(9) |
| complex karyotype | 15(27) |
| Other | 10(20) |
| Not done | 7(13) |
| Patient Status | |
| Primary refractory | 20(37) |
| Relapsed | 34(63) |

Figure 19 - Table 16

| Characteristic | Complete Remission | Treatment Failure |
|---|---|---|
| N | 11 | 13 |
| Age | | |
| median | 62.82 | 61.85 |
| range | 41-74 | 43-75 |
| Sex | | |
| Female | 7(63) | 7(53) |
| Male | 4(37) | 6(47) |
| White cell count x $10^9$ /L | | |
| median | 48.48 | 40.15 |
| range | 2.1-156 | 3.2-102 |
| BM blasts (%) | | |
| median | 45.5 | 50.6 |
| range | 21-91 | 21-88 |
| FAB no-(%) | | |
| M0-M1 | 3(27.5) | 4(30.4) |
| M2 | 3(27.5) | 1(7.6) |
| M4-M5 | 5(45) | 6(46) |
| Unknown | 0 | 2(16) |
| Cytogenetics no. (%) | | |
| normal karyotype | 6(55) | 5 (38) |
| complex karyotype* | 4(36) | 3 (23) |
| t(9;11) | 0 | 1 (7) |
| Other | 0 | 2 (16) |
| Not done | 1(9) | 2 (16) |
| Follow up (weeks) | | |
| median | 64.2 | 81.37 |
| range | 8-125 | 8-207 |

\* Complex karyotype is defined as 3 or more cytogenetic abnormalities
No statistically significant differences were observed between the two set of patients with regard to the characteristics shown in the table (t-Test and Fisher's exact test, SPSS).
The responses were evaluated 4 weeks after the induction chemotherapy (idarubicin 12mg/m$^2$ daily on days-1 to 3 and continuous infusion of cytarabine at 1500 mg/m$^2$ daily for 4 days) by bone marrow and peripheral blood examination. Complete remission (CR) was defined by the presence of < than 5% of blasts in the bone marrow aspirate, an absolute peripheral neutrophil count > 1 X $10^9$/l; platelets > 100 x $10^9$/l and no residual evidence of extramedullary disease.

Figure 20 – Table 17

| MicroRNA | SAM Score | Fold Change | FDR (%) |
|---|---|---|---|
| hsa-mir-183 | -3.04 | 5.50 | 0 |
| hsa-mir-208-prec | -2.99 | 3.20 | 0 |
| hsa-mir-184 | -2.96 | 5.60 | 0 |
| hsa-mir-29b | -2.92 | 3.10 | 0 |
| hsa-mir-194 | -2.89 | 4.30 | 0 |
| hsa-mir-183-prec | -2.73 | 3.20 | 0 |
| hsa-mir-205 | -2.71 | 3.10 | 0 |
| hsa-mir-337 | -2.66 | 4.30 | 0 |
| hsa-mir-199a | -2.65 | 3.50 | 0 |
| hsa-mir-199a-prec | -2.64 | 3.10 | 0 |
| hsa-mir-193 | -2.61 | 3.10 | 0 |
| hsa-mir-204 | -2.59 | 4.50 | 0 |
| hsa-mir-203 | -2.58 | 3.10 | 0 |
| hsa-mir-182 | -2.57 | 3.10 | 0 |
| hsa-mir-299-prec | -2.57 | 3.10 | 0 |
| hsa-mir-198 | -2.57 | 2.70 | 0 |
| hsa-mir-337-prec | -2.55 | 3.50 | 0 |
| hsa-mir-203-prec | -2.55 | 2.70 | 0 |
| hsa-mir-204-prec | -2.55 | 2.90 | 0 |
| hsa-mir-200c | -2.55 | 2.90 | 0 |
| hsa-mir-200cprec | -2.54 | 2.60 | 0 |
| hsa-mir-192 | -2.46 | 2.70 | 0 |
| hsa-mir-199b | -2.45 | 2.60 | 0 |
| hsa-mir-182-prec | -2.45 | 2.50 | 0 |
| hsa-mir-29c | -2.38 | 2.60 | 0 |

All miRNAs are down-regulated in patients who did not achieve complete remission after induction with Idarubicin and cytarabine.

Figure 21 – Table 18

MIR-29-BASED METHODS FOR THE DIAGNOSIS AND PROGNOSIS OF ACUTE MYELOID LEUKEMIA (AML)

CROSS-REFERENCE TO RELATED APPLICATIONS

This is a divisional application of U.S. Ser. No. 12/523,915 having a 37 CFR §1.371 filing date of Aug. 21, 2009, now U.S. Pat. No. 8,034,560 issued Oct. 11, 2011, which was a national stage application filed under 37 CFR 1.371 of international application PCT/US2008/001157 filed Jan. 29, 2008 which claims the priority to U.S. Provisional Application Ser. No. 60/898,578 filed Jan. 31, 2007, the entire disclosures of which are expressly incorporated herein by reference.

STATEMENT REGARDING FEDERALLY SPONSORED RESEARCH

This invention was made with government support under Grant Nos. PO1 CA76259, PO1 CA16058 and PO1 CA 81534, awarded by National Institutes of Health. The government has certain rights in this invention.

BACKGROUND OF THE INVENTION

Acute myeloid leukemia (AML) is a heterogeneous disorder that includes many entities with diverse genetic abnormalities and clinical features[1]. The pathogenesis is known for relatively few types of leukemia[2]. Patients with intermediate and poor risk cytogenetics represent the majority of AML; chemotherapy based regimens fail to cure most of these patients and stem cell transplantation is frequently the treatment choice[3-4]. Since allogeneic stem cell transplantation is not an option for many patients with high risk leukemia, there is a critical need to improve our understanding of the biology of these leukemias and to develop improved therapies.

Systematic high-throughput analysis of mRNA expression levels in AML has described new molecular subgroups of AML; some of these have been suggested to predict outcome[5-6]. Despite this progress, focusing on known genes will likely not suffice to uncover the molecular puzzle of AML. The integration of a whole genome approach including non-coding RNAs may lead to an improved understanding of AML biology.

MicroRNAs (miRNAs) are non-coding RNAs of 19-25 nucleotides in length that regulate gene expression by inducing translational inhibition or cleavage of their target mRNA through base pairing to partially or fully complementary sites[7]. The miRNAs are involved in critical biological processes, including development, cell differentiation, apoptosis and proliferation[8]. Recently, miRNA expression has been linked to hematopoiesis and cancer[9-11]. Calin et al. have shown deletions and down-regulation of miR-15a and miR-16-1 in chronic lymphocytic leukemia[12]. Several groups have reported changes in miRNA expression in large cell lymphoma[13] and pediatric Burkitt lymphoma[14]. More recently, it has been shown that over-expression of miR-155 in B cells of transgenic mice results in polyclonal B cell proliferation and B cell neoplasia[15]. These observations indicate that miRNAs are involved in the initiation and progression of human cancer.

As disclosed herein, miRNA microarrays are used to profile a large set of AML patients with predominately intermediate and poor prognosis to investigate the association of miRNA profiles with cytogenetic groups and clinical features.

Identification of microRNAs that are differentially-expressed in acute myeloid leukemia cancer cells would aid in diagnosing, prognosticating and treating leukemia. Furthermore, the identification of putative targets of these miRNAs would help to unravel their pathogenic role. In one broad aspect, there is provided herein provides novel methods and compositions for the diagnosis, prognosis and treatment of acute myeloid leukemia.

SUMMARY OF THE INVENTION

The present invention is based, in part, on the identification of an acute myeloid leukemia cancer-specific signature of miRNAs that are differentially-expressed in breast cancer cells, relative to normal control cells.

Accordingly, the invention encompasses methods of diagnosing whether a subject has, or is at risk for developing, acute myeloid leukemia (AML), comprising measuring the level of at least one miR gene product in a test sample from the subject, wherein an alteration in the level of the miR gene product in the test sample, relative to the level of a corresponding miR gene product in a control sample, is indicative of the subject either having, or being at risk for developing, AML.

In certain embodiments, at least one miR gene product is miR-29 or miR-181. In certain embodiments, the at least one miR gene product is miR-29b and/or miR-181b.

The level of the at least one miR gene product can be measured using a variety of techniques that are well known to those of skill in the art. In one embodiment, the level of the at least one miR gene product is measured using Northern blot analysis. In another embodiment, the level of the at least one miR gene product in the test sample is less than the level of the corresponding miR gene product in the control sample. Also, in another embodiment, the level of the at least one miR gene product in the test sample can be greater than the level of the corresponding miR gene product in the control sample.

The invention also provides methods of diagnosing a AML associated with one or more prognostic markers in a subject, comprising measuring the level of at least one miR gene product in a AML sample from the subject, wherein an alteration in the level of the at least one miR gene product in the test sample, relative to the level of a corresponding miR gene product in a control sample, is indicative of the subject having a AML associated with the one or more prognostic markers. In one embodiment, the level of the at least one miR gene product is measured by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal of at least one miRNA is indicative of the subject either having, or being at risk for developing, AML.

The invention also encompasses methods of treating CLL in a subject, wherein the signal of at least one miRNA, relative to the signal generated from the control sample, is de-regulated (e.g., down-regulated, up-regulated).

In certain embodiments, a microarray comprises miRNA-specific probe oligonucleotides for one or more miRNAs selected from the group consisting of miR-29 or miR-181 and combinations thereof.

The invention also encompasses methods of diagnosing whether a subject has, or is at risk for developing, a AML associated with one or more adverse prognostic markers in a subject, by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal is indicative of the subject either having, or being at risk for developing, the cancer.

The invention also encompasses methods of treating AML in a subject who has AML in which at least one miR gene product is down-regulated or up-regulated in the cancer cells of the subject relative to control cells. When the at least one miR gene product is down-regulated in the cancer cells, the method comprises administering to the subject an effective amount of at least one isolated miR gene product, such that proliferation of cancer cells in the subject is inhibited. When the at least one miR gene product is up-regulated in the cancer cells, the method comprises administering to the subject an effective amount of at least one compound for inhibiting expression of the at least one miR gene product, such that proliferation of cancer cells in the subject is inhibited. In certain embodiments, the at least one isolated miR gene product is selected miR-29, miR-181 and combinations thereof.

In related embodiments, the invention provides methods of treating AML in a subject, comprising: determining the amount of at least one miR gene product in AML cells, relative to control cells; and altering the amount of miR gene product expressed in the AML cells by: administering to the subject an effective amount of at least one isolated miR gene product, if the amount of the miR gene product expressed in the cancer cells is less than the amount of the miR gene product expressed in control cells; or administering to the subject an effective amount of at least one compound for inhibiting expression of the at least one miR gene product, if the amount of the miR gene product expressed in the cancer cells is greater than the amount of the miR gene product expressed in control cells, such that proliferation of cancer cells in the subject is inhibited. In certain embodiments, at least one isolated miR gene product is selected from the group consisting of miR-29, miR-181, and combinations thereof.

The invention further provides pharmaceutical compositions for treating AML, comprising at least one isolated miR gene product and a pharmaceutically-acceptable carrier. In a particular embodiment, the pharmaceutical compositions the at least one isolated miR gene product corresponds to a miR gene product that is down-regulated in AML cells relative to suitable control cells. In particular embodiments, the pharmaceutical composition is selected from the group consisting of miR-29, miR-181 and combinations thereof. In another particular embodiment, the pharmaceutical composition comprises at least one miR expression inhibitor compound and a pharmaceutically-acceptable carrier. Also, in a particular embodiment, the pharmaceutical composition comprises at least one miR expression inhibitor compound is specific for a miR gene product that is up-regulated in AML cells relative to suitable control cells.

In other embodiments, the present invention provides methods of identifying an anti-AML agent, comprising providing a test agent to a cell and measuring the level of at least one miR gene product associated with decreased expression levels in AML cells, wherein an increase in the level of the miR gene product in the cell, relative to a suitable control cell, is indicative of the test agent being an anti-AML agent. In certain embodiments, the miR gene product is selected from the group consisting of at least one miR gene product is selected from the group consisting of the miRNAs as shown in any one of FIGS. 5-6, 8-18 and 21 (Tables 1-2, 5-15 and 18). In a particular embodiment, least one miR gene product is selected from the group consisting of miR-20, miR-25, miR-191, miR-199a, and miR-199b and combinations thereof.

The present invention also provides methods of identifying an anti-AML agent, comprising providing a test agent to a cell and measuring the level of at least one miR gene product associated with increased expression levels in AML cells, wherein an decrease in the level of the miR gene product in the cell, relative to a suitable control cell, is indicative of the test agent being an anti-AML agent. In a particular embodiment, the miR gene product is selected from the group consisting of miR-29, miR-181 and combinations thereof.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

FIG. 1A. MicroRNA (miRNA) expression of 6 AML samples with respect to CD34+ progenitors. Results are presented as fold change of the miRNA expression in AML samples with respect to CD34+ expression values, after normalization (Ct) with let-7i and $2^{\Delta Ct}$ conversion[18] (thin bars represent standard deviations).

FIG. 1B. Validation of the microarrays data using qRT-PCR. Scatter plot showing the negative correlation between the miRNA micro array s expression values (2 log) and the normalized qRT-PCR OCt values (log scale) for each sample (Pearson correlation coefficient R=0.88 p<0.001). The solid pink line represents the predicted Y. The lower the qRT-PCR (Ct values), the higher the expression level of the miRNA. For example, the points at the bottom right have low ΔCt values (high expression) and correspond with high micro array (chip) values.

FIG. 1C. mRNA expression in mature and hematopoietic committed precursors with respect to CD34+ stem cells. The results are presented as fold change in the average miRNA expression of the different mature and committed precursors with respect to that of CD34+ cells after normalization with 18S and $2^{\Delta Ct}$ conversion.

FIG. 1D. Average qRT-PCR expression of miR-181 b in AML samples grouped according the FAB classification; the numbers of patient samples in each category are as follows; M0-M1 (6), M2 (8) and M 6M7 (5).

FIG. 1E. Average miR-10 qRT-PCR expression in AML patients with normal karyotype (10) vs. other abnormal karyotype (26).

FIG. 1F. Average expression of miR-126 in patients with complex karyotype (6) and in patients with other cytogenetic abnormalities (22) by qRT-PCR. The miRNA expression between the different groups was compared by using t-Test (SPSS).

Figure 2A:
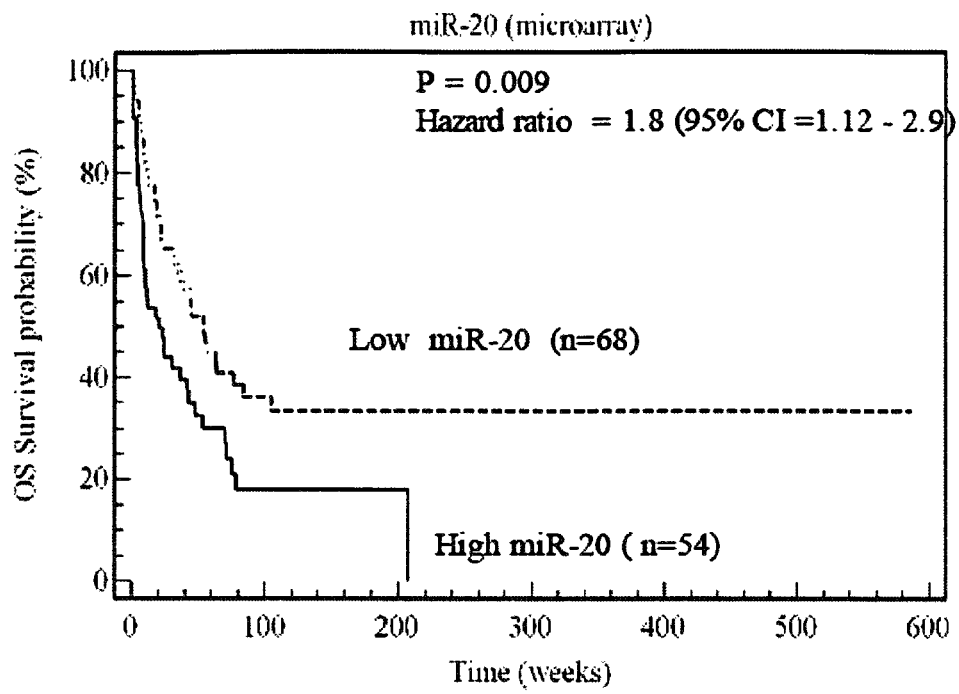
FIGS. 2A-D. MicroRNAs associated with overall survival in newly diagnosed patients with AML. Kaplan-Meier estimates of overall survival for 122 AML patients with high or low expression of miR-20 (FIG. 2A) and miR-25 (FIG. 2B) detected by micro arrays. The log-rank test was used to compare differences between survival curves. An independent set of 36 AML patients with similar clinical characteristics (FIG.
Figure 2B:
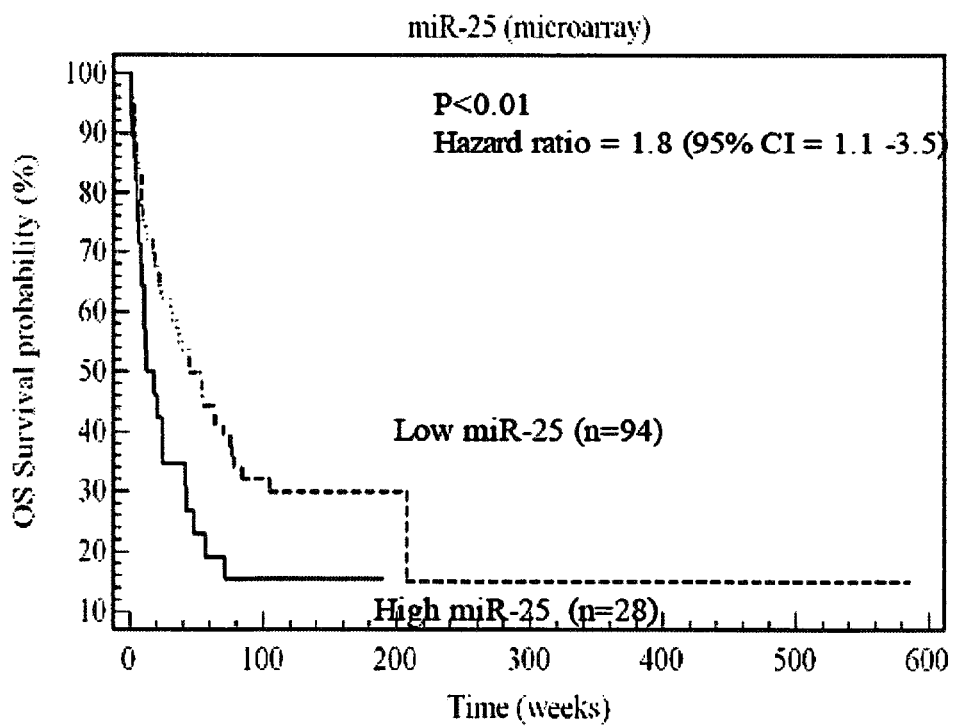
Figure 2C:
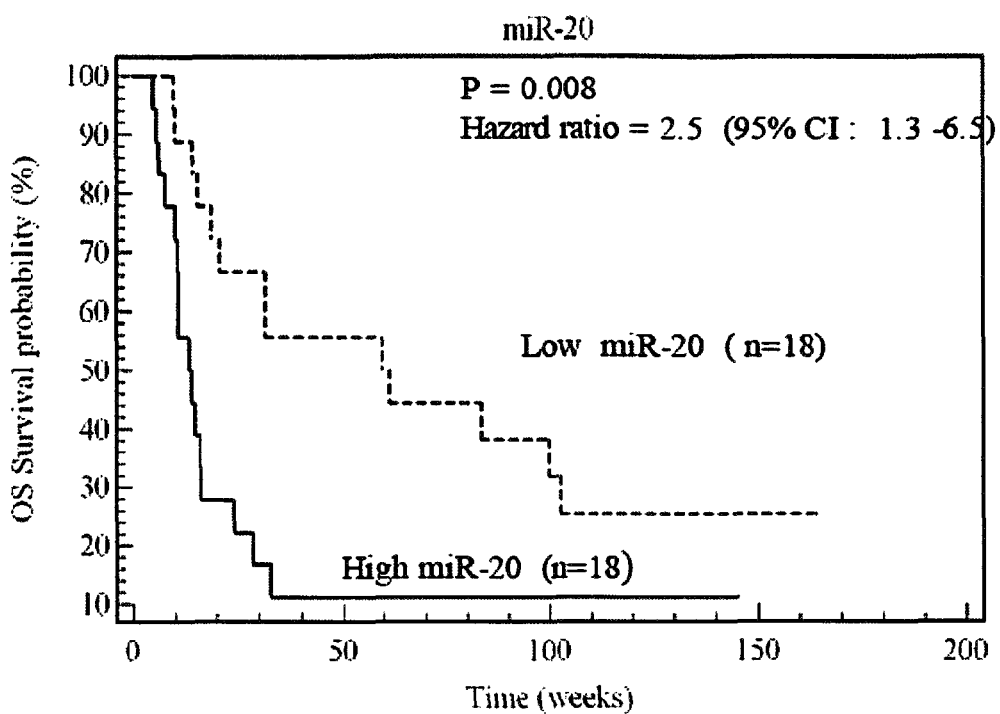
Figure 2D:
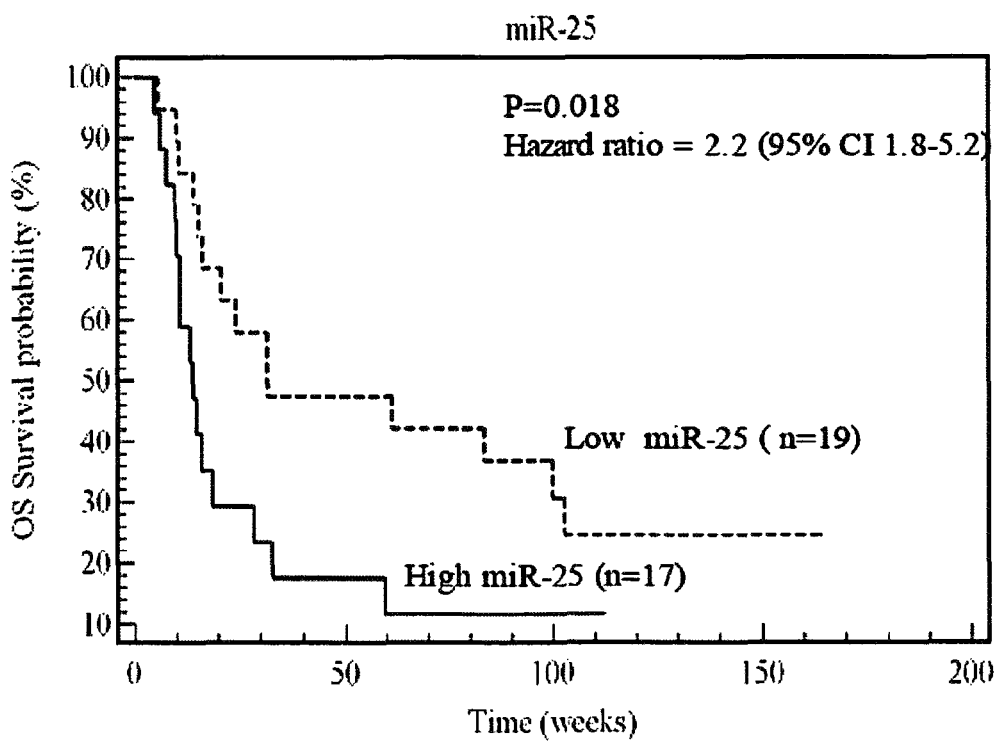

4 (Table 1)) was used to validate the outcome predictive power of miR-20 and miR-25 by using a different technology (miRNA qRT-PCR). Kaplan-Meier estimates of overall survival for the 36 AML patients with high or low expression of miR-20 (FIG. 2C) and miR-25 (FIG. 2D) detected by qRT-PCR are shown. Hazard ratios with 95% confidence intervals (CI 95%) were obtained by the Kaplan-Meier method.

Figure 3A:
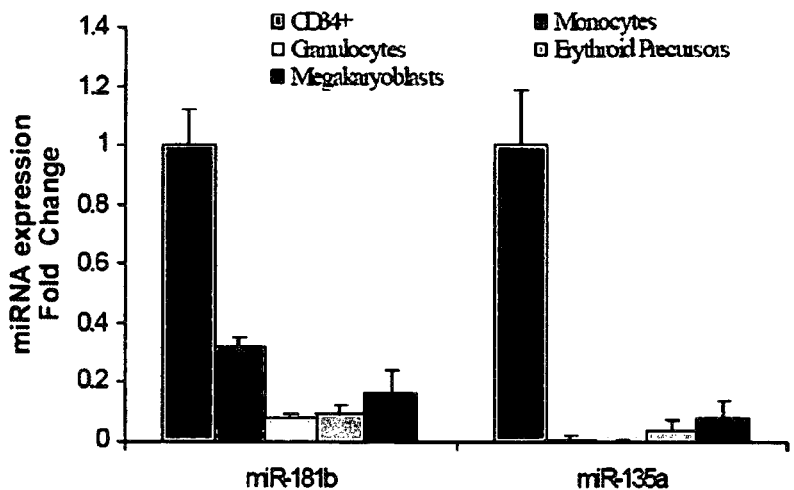

FIG. 3A. Average qRT-PCR of miR-181b and miR-135a expression in bone marrow erythrocytic/megakaryocytic precursors and peripheral blood mature granulocytes/monocytes obtained from four different healthy donors. Results are shown as the fold change in the miRNA expression in the different lineages with respect to that of miR-181b and miR-135b in four CD34+ cells.

Figure 3B:
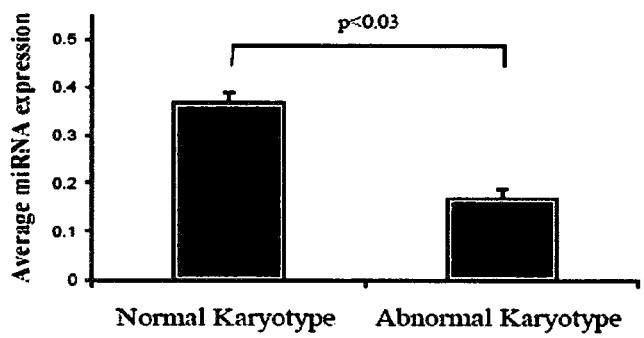

FIG. 3B. Average qRT-PCR expression values of miR-30c in 10 patients with normal karyotype and in 22 patients with abnormal karyotype. The miRNA expression values from the two groups (Normal vs. abnormal karyotype) were compared using t-Test (SPSS).

Figure 3C:
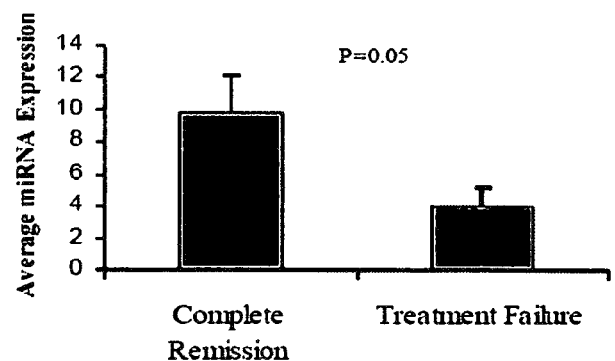

FIG. 3C. Average miR-29b expression in AML patients who received induction chemotherapy with idarubicin and cytarabine by qRT-PCR in 12 independent patients with newly diagnosed AML that achieve complete remission (6) or have failure to achieve induction chemotherapy (6). The miRNA expression values from the two groups (CR vs. failure) were compared using t-Test (SPSS).

FIG. 4. Table 1. Clinical and cytogenetics characterizations of 158 newly diagnosed patients with AML.

FIG. 5. Table 2. MicroRNAs associated with FAB classification and cytogenetics.

FIG. 6. Table 3. MicroRNAs associated with overall survival in 122 patients with AML.

FIG. 7. Table 4. Housekeeping gene probes used in the normalization of microarray data.

FIG. 8. Table 5. mRNAs differentially expressed between CD 34+ cells and the 122 patients with AML.

FIG. 9 (Table 6). mRNAs differentially expressed in AML FAB M0-M1 compared with others AML FAB subtypes.

FIG. 10. Table 7. mRNAs differentially expressed in AML FAB M3 [t (15; 17)].

FIG. 11. Table 8. mRNAs differentially expressed in AML FAB M4 and M5 compared with other AML.

FIG. 12. Table 9. mRNAs differentially expressed in AML FAB M6 and M7 compared with other AML.

FIG. 13. Table 10. mRNAs associated with high WBC, and peripheral blood (PB) and bone marrow (BM) blasts.

FIG. 14. Table 11. mRNAs differentially expressed in normal karyotype AML compared with other AML.

FIG. 15. Table 12. mRNAs associated with 11q23 rearrangements.

FIG. 16. Table 13. mRNAs differentially expressed in patients with complex karyotype compared with non-complex or normal karyotype.

FIG. 17. Table 14. mRNAs associated with chromosome 7.

FIG. 18. Table 15. mRNAs associated with trisomy 8.

FIG. 19. Table 16. Characteristics of 54 patients with AML at first relapse after initial induction chemotherapy or primary refractory disease.

FIG. 20. Table 17. Clinical characteristics of the 24 patients treated with idarubicin and cytarabine.

FIG. 21. Table 18. mRNAs associated with response to Idarubicin and cytarabine.

DESCRIPTION OF THE INVENTION

The present invention is based, in part, on the identification of particular microRNAs having altered expression in acute myeloid leukemia (AML) cancer cells relative to normal control cells, and on association of these microRNAs with particular diagnostic, prognostic and therapeutic features.

As used herein interchangeably, a "miR gene product," "microRNA," "miR," or "miRNA" refers to the unprocessed or processed RNA transcript from a miR gene. As the miR gene products are not translated into protein, the term "miR gene products" does not include proteins. The unprocessed miR gene transcript is also called a "miR precursor," and typically comprises an RNA transcript of about 70-100 nucleotides in length. The miR precursor can be processed by digestion with an RNAse (for example, Dicer, Argonaut, RNAse III (e.g., *E. coli* RNAse III)) into an active 19-25 nucleotide RNA molecule. This active 19-25 nucleotide RNA molecule is also called the "processed" miR gene transcript or "mature" miRNA.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having to be processed from the miR precursor. When a microRNA is referred to herein by name, the name corresponds to both the precursor and mature forms, unless otherwise indicated.

The present invention encompasses methods of diagnosing whether a subject has, or is at risk for developing, AML, comprising measuring the level of at least one miR gene product in a test sample from the subject and comparing the level of the miR gene product in the test sample to the level of a corresponding miR gene product in a control sample. As used herein, a "subject" can be any mammal that has, or is suspected of having, AML. In a preferred embodiment, the subject is a human who has, or is suspected of having, AML.

The level of at least one miR gene product can be measured in cells of a biological sample obtained from the subject. For example, a tissue sample can be removed from a subject suspected of having AML by conventional biopsy techniques. In another embodiment, a blood sample can be removed from the subject, and white blood cells can be isolated for DNA extraction by standard techniques. The blood or tissue sample is preferably obtained from the subject prior to initiation of radiotherapy, chemotherapy or other therapeutic treatment. A corresponding control tissue or blood sample, or a control reference sample, can be obtained from unaffected tissues of the subject, from a normal human individual or population of normal individuals, or from cultured cells corresponding to the majority of cells in the subject's sample. The control tissue or blood sample is then processed along with the sample from the subject, so that the levels of miR gene product produced from a given miR gene in cells from the subject's sample can be compared to the corresponding miR gene product levels from cells of the control sample. Alternatively, a reference sample can be obtained and processed separately (e.g., at a different time) from the test sample and the level of a miR gene product produced from a given miR gene in cells from the test sample can be compared to the corresponding miR gene product level from the reference sample.

In one embodiment, the level of the at least one miR gene product in the test sample is greater than the level of the corresponding miR gene product in the control sample (i.e., expression of the miR gene product is "up-regulated"). As used herein, expression of a miR gene product is "up-regulated" when the amount of miR gene product in a cell or tissue sample from a subject is greater than the amount of the same gene product in a control cell or tissue sample. In another embodiment, the level of the at least one miR gene product in the test sample is less than the level of the corresponding miR gene product in the control sample (i.e., expression of the miR gene product is "down-regulated"). As used herein, expression of a miR gene is "down-regulated" when the amount of miR gene product produced from that gene in a cell or tissue sample from a subject is less than the amount produced from the same gene in a control cell or tissue sample. The relative miR gene expression in the control and normal samples can be determined with respect to one or more RNA expression standards. The standards can comprise, for example, a zero miR gene expression level, the miR gene expression level in a standard cell line, the miR gene expression level in unaffected tissues of the subject, or the average level of miR gene expression previously obtained for a population of normal human controls.

An alteration (i.e., an increase or decrease) in the level of a miR gene product in the sample obtained from the subject, relative to the level of a corresponding miR gene product in a control sample, is indicative of the presence of AML cancer in the subject. In one embodiment, the level of at least one miR gene product in the test sample is greater than the level of the corresponding miR gene product in the control sample. In another embodiment, the level of at least one miR gene product in the test sample is less than the level of the corresponding miR gene product in the control sample.

In a certain embodiment, the at least one miR gene product is selected from the groups as shown in the Tables and Figures herein.

The level of a miR gene product in a sample can be measured using any technique that is suitable for detecting RNA expression levels in a biological sample. Suitable techniques (e.g., Northern blot analysis, RT-PCR, in situ hybridization) for determining RNA expression levels in a biological sample (e.g., cells, tissues) are well known to those of skill in the art. In a particular embodiment, the level of at least one miR gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Suitable probes (e.g., DNA probes, RNA probes) for Northern blot hybridization of a given miR gene product can be produced from the nucleic acid sequences provided in the Tables herein and include, but are not limited to, probes having at least about 70%, 75%, 80%, 85%, 90%, 95%, 98% or 99% complementarity to a miR gene product of interest, as well as probes that have complete complementarity to a miR gene product of interest. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are incorporated herein by reference.

For example, the nucleic acid probe can be labeled with, e.g., a radionuclide, such as $^{3}H$, $^{32}P$, $^{33}P$, $^{14}C$, or $^{35}S$; a heavy metal; a ligand capable of functioning as a specific binding pair member for a labeled ligand (e.g., biotin, avidin or an antibody); a fluorescent molecule; a chemiluminescent molecule; an enzyme or the like.

Probes can be labeled to high specific activity by either the nick translation method of Rigby et al. (1977), J. Mol. Biol. 113:237-251 or by the random priming method of Fienberg et al. (1983), Anal. Biochem. 132:6-13, the entire disclosures of which are incorporated herein by reference. The latter is the method of choice for synthesizing $^{32}P$-labeled probes of high specific activity from single-stranded DNA or from RNA templates. For example, by replacing preexisting nucleotides with highly radioactive nucleotides according to the nick translation method, it is possible to prepare $^{32}P$-labeled nucleic acid probes with a specific activity well in excess of $10^8$ cpm/microgram. Autoradiographic detection of hybridization can then be performed by exposing hybridized filters to photographic film. Densitometric scanning of the photographic films exposed by the hybridized filters provides an accurate measurement of miR gene transcript levels. Using another approach, miR gene transcript levels can be quantified by computerized imaging systems, such as the Molecular Dynamics 400-B 2D Phosphorimager available from Amersham Biosciences, Piscataway, N.J.

Where radionuclide labeling of DNA or RNA probes is not practical, the random-primer method can be used to incorporate an analogue, for example, the dTTP analogue 5-(N-(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference. Suitable probes for in situ hybridization of a given miR gene product can be produced from the nucleic acid sequences provided in the Tables herein, and include, but are not limited to, probes having at least about 70%, 75%, 80%, 85%, 90%, 95%, 98% or 99% complementarity to a miR gene product of interest, as well as probes that have complete complementarity to a miR gene product of interest, as described above.

The relative number of miR gene transcripts in cells can also be determined by reverse transcription of miR gene transcripts, followed by amplification of the reverse-transcribed transcripts by polymerase chain reaction (RT-PCR). The levels of miR gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). Methods for performing quantitative and semi-quantitative RT-PCR, and variations thereof, are well known to those of skill in the art.

In some instances, it may be desirable to simultaneously determine the expression level of a plurality of different miR gene products in a sample. In other instances, it may be desirable to determine the expression level of the transcripts of all known miR genes correlated with a cancer. Assessing cancer-specific expression levels for hundreds of miR genes or gene products is time consuming and requires a large amount of total RNA (e.g., at least 20 μg for each Northern blot) and autoradiographic techniques that require radioactive isotopes.

To overcome these limitations, an oligolibrary, in microchip format (i.e., a microarray), may be constructed containing a set of oligonucleotide (e.g., oligodeoxynucleotide) probes that are specific for a set of miR genes. Using such a microarray, the expression level of multiple microRNAs in a biological sample can be determined by reverse transcribing the RNAs to generate a set of target oligodeoxynucleotides, and hybridizing them to probe the oligonucleotides on the microarray to generate a hybridization, or expression, profile. The hybridization profile of the test sample can then be compared to that of a control sample to determine which microRNAs have an altered expression level in AML cancer cells. As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "miR-specific probe oligonucleotide" or "probe oligonucleotide specific for a miR" is meant a probe oligonucleotide that has a sequence selected to hybridize to a specific miR gene product, or to a reverse transcript of the specific miR gene product.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal tissue may be distinguished from AML cells, and within AML cells, different prognosis states (for example, good or poor long term survival prospects) may be determined. By comparing expression profiles of AML cells in different states, information regarding which genes are important (including both up- and down-regulation of genes) in each of these states is obtained. The identification of sequences that are differentially expressed in AML cells or normal cells, as well as differential expression resulting in different prognostic outcomes, allows the use of this information in a number of ways. For example, a particular treatment regime may be evaluated (e.g., to determine whether a chemotherapeutic drug acts to improve the long-term prognosis in a particular patient). Similarly, diagnosis may be done or confirmed by comparing patient samples with known expression profiles. Furthermore, these gene expression profiles (or individual genes) allow screening of drug candidates that suppress the AML expression profile or convert a poor prognosis profile to a better prognosis profile.

Accordingly, the invention provides methods of diagnosing whether a subject has, or is at risk for developing, AML, comprising reverse transcribing RNA from a test sample obtained from the subject to provide a set of target oligodeoxynucleotides, hybridizing the target oligodeoxynucleotides to a microarray comprising miRNA-specific probe oligonucleotides to provide a hybridization profile for the test sample, and comparing the test sample hybridization profile to a hybridization profile generated from a control sample, wherein an alteration in the signal of at least one miRNA is indicative of the subject either having, or being at risk for developing, AML. In one embodiment, the microarray comprises miRNA-specific probe oligonucleotides for a substantial portion of all known human miRNAs.

In a particular embodiment, the microarray comprises miRNA-specific probe oligonucleotides for one or more miRNAs selected from the group consisting of the miRNAs as shown in any one of FIGS. 5-6, 8-18 and 21 (Tables 1-2, 5-15 and 18). In one embodiment, at least one miR gene product is selected from the group consisting of miR-20, miR-25, miR-191, miR-199a, and miR-199b and combinations thereof.

The microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs and other RNAs (e.g., rRNAs, mRNAs) from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/30% formamide at 25° C. for 18 hours, followed by washing in 0.75×TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRs, in the patient sample. According to one embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding miR in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 μg of total RNA. The relatively limited number of miRNAs (a few hundred per species) allows the construction of a common microarray for several species, with distinct oligonucleotide probes for each.

Such a tool would allow for analysis of trans-species expression for each known miR under various conditions.

In addition to use for quantitative expression level assays of specific miRs, a microchip containing miRNA-specific probe oligonucleotides corresponding to a substantial portion of the miRNome, preferably the entire miRNome, may be employed to carry out miR gene expression profiling, for analysis of miR expression patterns. Distinct miR signatures can be associated with established disease markers, or directly with a disease state.

According to the expression profiling methods described herein, total RNA from a sample from a subject suspected of having a cancer (e.g., AML) is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile generated from a normal, e.g., noncancerous, control sample. An alteration in the signal is indicative of the presence of, or propensity to develop, cancer in the subject.

Other techniques for measuring miR gene expression are also within the skill in the art, and include various techniques for measuring rates of RNA transcription and degradation.

The invention also provides methods of determining the prognosis of a subject with AML cancer, comprising measuring the level of at least one miR gene product, which is associated with a particular prognosis in AML (e.g., a good or positive prognosis, a poor or adverse prognosis), in a test sample from the subject. According to these methods, an alteration in the level of a miR gene product that is associated with a particular prognosis, in the test sample, as compared to the level of a corresponding miR gene product in a control sample, is indicative of the subject having AML with a particular prognosis. In one embodiment, the miR gene product is associated with an adverse (i.e., poor) prognosis. Examples of an adverse prognosis include, but are not limited to, low survival rate and rapid disease progression.

In certain embodiments, the level of the at least one miR gene product is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample.

Without wishing to be bound by any one theory, it is believed that alterations in the level of one or more miR gene products in cells can result in the deregulation of one or more intended targets for these miRs, which can lead to the formation of AML. Therefore, altering the level of the miR gene product (e.g., by decreasing the level of a miR that is up-regulated in AML cancer cells, by increasing the level of a miR that is down-regulated in AML cancer cells) may successfully treat the AML cancer.

Accordingly, the present invention encompasses methods of treating AML in a subject, wherein at least one miR gene product is deregulated (e.g., down-regulated, up-regulated) in the cells (e.g., AML cancer cells) of the subject. In one embodiment, the level of at least one miR gene product in a test sample (e.g., AML cancer sample) is greater than the level of the corresponding miR gene product in a control sample. In another embodiment, the level of at least one miR gene product in a test sample (e.g., AML cancer sample) is less than the level of the corresponding miR gene product in a control sample. When the at least one isolated miR gene product is down-regulated in the AML cancer cells, the method comprises administering an effective amount of the at least one isolated miR gene product, or an isolated variant or biologically-active fragment thereof, such that proliferation of cancer cells in the subject is inhibited. For example, when a miR gene product is down-regulated in a cancer cell in a subject, administering an effective amount of an isolated miR gene product to the subject can inhibit proliferation of the cancer cell. The isolated miR gene product that is administered to the subject can be identical to an endogenous wild-type miR gene product (e.g., a miR gene product shown in the Tables herein) that is down-regulated in the cancer cell or it can be a variant or biologically-active fragment thereof.

As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of expression of a target RNA molecule (e.g., inhibiting translation of a target RNA molecule, modulating the stability of a target RNA molecule, inhibiting processing of a target RNA molecule) and inhibition of a cellular process associated with AML (e.g., cell differentiation, cell growth, cell death). These variants include species variants and variants that are the consequence of one or more mutations (e.g., a substitution, a deletion, an insertion) in a miR gene. In certain embodiments, the variant is at least about 70%, 75%, 80%, 85%, 90%, 95%, 98%, or 99% identical to a corresponding wild-type miR gene product.

As defined herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of expression of a target RNA molecule and inhibition of a cellular process associated with AML. In certain embodiments, the biologically-active fragment is at least about 5, 7, 10, 12, 15, or 17 nucleotides in length. In a particular embodiment, an isolated miR gene product can be administered to a subject in combination with one or more additional anti-cancer treatments. Suitable anti-cancer treatments include, but are not limited to, chemotherapy, radiation therapy and combinations thereof (e.g., chemoradiation).

When the at least one isolated miR gene product is up-regulated in the cancer cells, the method comprises administering to the subject an effective amount of a compound that inhibits expression of the at least one miR gene product, such that proliferation of AML cancer cells is inhibited. Such compounds are referred to herein as miR gene expression-inhibition compounds. Examples of suitable miR gene expression-inhibition compounds include, but are not limited to, those described herein (e.g., double-stranded RNA, anti-sense nucleic acids and enzymatic RNA molecules). In a particular embodiment, a miR gene expression-inhibiting compound can be administered to a subject in combination with one or more additional anti-cancer treatments. Suitable anti-cancer treatments include, but are not limited to, chemotherapy, radiation therapy and combinations thereof (e.g., chemoradiation).

In a certain embodiment, the isolated miR gene product that is deregulated in AML cancer is selected from the group consisting of the miRNAs as shown in any one of FIGS. 5-6, 8-18 and 21 (Tables 1-2, 5-15 and 18).

In a particular embodiment, the at least one miR gene product is selected from the group consisting of miR-20, miR-25, miR-191, miR-199a, and miR-199b and combinations thereof.

The terms "treat", "treating" and "treatment", as used herein, refer to ameliorating symptoms associated with a disease or condition, for example, AML cancer, including preventing or delaying the onset of the disease symptoms, and/or lessening the severity or frequency of symptoms of the disease or condition. The terms "subject" and "individual" are defined herein to include animals, such as mammals, including, but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

As used herein, an "effective amount" of an isolated miR gene product is an amount sufficient to inhibit proliferation of a cancer cell in a subject suffering from AML cancer. One skilled in the art can readily determine an effective amount of a miR gene product to be administered to a given subject, by taking into account factors, such as the size and weight of the subject; the extent of disease penetration; the age, health and sex of the subject; the route of administration; and whether the administration is regional or systemic.

For example, an effective amount of an isolated miR gene product can be based on the approximate weight of a tumor mass to be treated. The approximate weight of a tumor mass can be determined by calculating the approximate volume of the mass, wherein one cubic centimeter of volume is roughly equivalent to one gram. An effective amount of the isolated miR gene product based on the weight of a tumor mass can be in the range of about 10-500 micrograms/gram of tumor mass. In certain embodiments, the tumor mass can be at least about 10 micrograms/gram of tumor mass, at least about 60 micrograms/gram of tumor mass or at least about 100 micrograms/gram of tumor mass.

An effective amount of an isolated miR gene product can also be based on the approximate or estimated body weight of a subject to be treated. Preferably, such effective amounts are administered parenterally or enterally, as described herein. For example, an effective amount of the isolated miR gene product that is administered to a subject can range from about 5-3000 micrograms/kg of body weight, from about 700-1000 micrograms/kg of body weight, or greater than about 1000 micrograms/kg of body weight.

One skilled in the art can also readily determine an appropriate dosage regimen for the administration of an isolated miR gene product to a given subject. For example, a miR gene product can be administered to the subject once (e.g., as a single injection or deposition). Alternatively, a miR gene product can be administered once or twice daily to a subject for a period of from about three to about twenty-eight days, more particularly from about seven to about ten days. In a particular dosage regimen, a miR gene product is administered once a day for seven days. Where a dosage regimen comprises multiple administrations, it is understood that the effective amount of the miR gene product administered to the subject can comprise the total amount of gene product administered over the entire dosage regimen.

As used herein, an "isolated" miR gene product is one that is synthesized, or altered or removed from the natural state through human intervention. For example, a synthetic miR gene product, or a miR gene product partially or completely separated from the coexisting materials of its natural state, is considered to be "isolated." An isolated miR gene product can exist in a substantially-purified form, or can exist in a cell into which the miR gene product has been delivered. Thus, a miR gene product that is deliberately delivered to, or expressed in, a cell is considered an "isolated" miR gene product. A miR gene product produced inside a cell from a miR precursor molecule is also considered to be an "isolated" molecule. According to the invention, the isolated miR gene products described herein can be used for the manufacture of a medicament for treating AML cancer in a subject (e.g., a human).

Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Alternatively, the miR gene products can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible or regulatable promoters for expression of the miR gene products in cancer cells.

The miR gene products that are expressed from recombinant plasmids can be isolated from cultured cell expression systems by standard techniques. The miR gene products that are expressed from recombinant plasmids can also be delivered to, and expressed directly in, the cancer cells. The use of recombinant plasmids to deliver the miR gene products to cancer cells is discussed in more detail below.

The miR gene products can be expressed from a separate recombinant plasmid, or they can be expressed from the same recombinant plasmid. In one embodiment, the miR gene products are expressed as RNA precursor molecules from a single plasmid, and the precursor molecules are processed into the functional miR gene product by a suitable processing system, including, but not limited to, processing systems extant within a cancer cell. Other suitable processing systems include, e.g., the in vitro *Drosophila* cell lysate system (e.g., as described in U.S. Published Patent Application No. 2002/0086356 to Tuschl et al., the entire disclosure of which is incorporated herein by reference) and the *E. coli* RNAse III system (e.g., as described in U.S. Published Patent Application No. 2004/0014113 to Yang et al., the entire disclosure of which is incorporated herein by reference).

Selection of plasmids suitable for expressing the miR gene products, methods for inserting nucleic acid sequences into the plasmid to express the gene products, and methods of delivering the recombinant plasmid to the cells of interest are within the skill in the art. See, for example, Zeng et al. (2002), Molecular Cell 9:1327-1333; Tuschl (2002), Nat. Biotechnol, 20:446-448; Brummelkamp et al. (2002), Science 296:550-553; Miyagishi et al. (2002), Nat. Biotechnol. 20:497-500;

Paddison et al. (2002), Genes Dev. 16:948-958; Lee et al. (2002), Nat. Biotechnol. 20:500-505; and Paul et al. (2002), Nat. Biotechnol. 20:505-508, the entire disclosures of which are incorporated herein by reference.

In one embodiment, a plasmid expressing the miR gene products comprises a sequence encoding a miR precursor RNA under the control of the CMV intermediate-early promoter. As used herein, "under the control" of a promoter means that the nucleic acid sequences encoding the miR gene product are located 3' of the promoter, so that the promoter can initiate transcription of the miR gene product coding sequences.

The miR gene products can also be expressed from recombinant viral vectors. It is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in cancer cells. The use of recombinant viral vectors to deliver the miR gene products to cancer cells is discussed in more detail below.

The recombinant viral vectors of the invention comprise sequences encoding the miR gene products and any suitable promoter for expressing the RNA sequences. Suitable promoters include, but are not limited to, the U6 or H1 RNA pol III promoter sequences, or the cytomegalovirus promoters. Selection of other suitable promoters is within the skill in the art. The recombinant viral vectors of the invention can also comprise inducible or regulatable promoters for expression of the miR gene products in a cancer cell.

Any viral vector capable of accepting the coding sequences for the miR gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art; see, e.g., Rabinowitz, J. E., et al. (2002), J. Virol. 76:791-801, the entire disclosure of which is incorporated herein by reference.

Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Dornburg (1995), Gene Therap. 2:301-310; Eglitis (1988), Biotechniques 6:608-614; Miller (1990), Hum. Gene Therap. 1:5-14; and Anderson (1998), Nature 392:25-30, the entire disclosures of which are incorporated herein by reference.

Particularly suitable viral vectors are those derived from AV and AAV. A suitable AV vector for expressing the miR gene products, a method for constructing the recombinant AV vector, and a method for delivering the vector into target cells, are described in Xia et al. (2002), Nat. Biotech. 20:1006-1010, the entire disclosure of which is incorporated herein by reference. Suitable AAV vectors for expressing the miR gene products, methods for constructing the recombinant AAV vector, and methods for delivering the vectors into target cells are described in Samulski et al. (1987), J. Virol. 61:3096-3101; Fisher et al. (1996), J. Virol., 70:520-532; Samulski et al. (1989), J. Virol. 63:3822-3826; U.S. Pat. No. 5,252,479; U.S. Pat. No. 5,139,941; International Patent Application No. WO 94/13788; and International Patent Application No. WO 93/24641, the entire disclosures of which are incorporated herein by reference. In one embodiment, the miR gene products are expressed from a single recombinant AAV vector comprising the CMV intermediate early promoter.

In a certain embodiment, a recombinant AAV viral vector of the invention comprises a nucleic acid sequence encoding a miR precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR sequences from the vector, the polyT termination signals act to terminate transcription.

In other embodiments of the treatment methods of the invention, an effective amount of at least one compound that inhibits miR expression can be administered to the subject. As used herein, "inhibiting miR expression" means that the production of the precursor and/or active, mature form of miR gene product after treatment is less than the amount produced prior to treatment. One skilled in the art can readily determine whether miR expression has been inhibited in a cancer cell, using, for example, the techniques for determining miR transcript level discussed herein. Inhibition can occur at the level of gene expression (i.e., by inhibiting transcription of a miR gene encoding the miR gene product) or at the level of processing (e.g., by inhibiting processing of a miR precursor into a mature, active miR).

As used herein, an "effective amount" of a compound that inhibits miR expression is an amount sufficient to inhibit proliferation of a cancer cell in a subject suffering from a cancer (e.g., AML cancer). One skilled in the art can readily determine an effective amount of a miR expression-inhibiting compound to be administered to a given subject, by taking into account factors, such as the size and weight of the subject; the extent of disease penetration; the age, health and sex of the subject; the route of administration; and whether the administration is regional or systemic.

For example, an effective amount of the expression-inhibiting compound can be based on the approximate weight of a tumor mass to be treated, as described herein. An effective amount of a compound that inhibits miR expression can also be based on the approximate or estimated body weight of a subject to be treated, as described herein.

One skilled in the art can also readily determine an appropriate dosage regimen for administering a compound that inhibits miR expression to a given subject, as described herein.

Suitable compounds for inhibiting miR gene expression include double-stranded RNA (such as short- or small-interfering RNA or "siRNA"), antisense nucleic acids, and enzymatic RNA molecules, such as ribozymes. Each of these compounds can be targeted to a given miR gene product and interfere with the expression (e.g., by inhibiting translation, by inducing cleavage and/or degradation) of the target miR gene product.

For example, expression of a given miR gene can be inhibited by inducing RNA interference of the miR gene with an isolated double-stranded RNA ("dsRNA") molecule which has at least 90%, for example at least 95%, at least 98%, at least 99%, or 100%, sequence homology with at least a portion of the miR gene product. In a particular embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence that is substantially identical to a nucleic acid sequence contained within the target miR gene product.

As used herein, a nucleic acid sequence in an siRNA that is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in certain embodiments, the siRNA comprises at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated miR gene products. Exemplary methods for producing and testing dsRNA or siRNA molecules are described in U.S. Published Patent Application No. 2002/0173478 to Gewirtz and in U.S. Published Patent Application No. 2004/0018176 to Reich et al., the entire disclosures of both of which are incorporated herein by reference.

Expression of a given miR gene can also be inhibited by an antisense nucleic acid. As used herein, an "antisense nucleic acid" refers to a nucleic acid molecule that binds to target RNA by means of RNA-RNA, RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, peptide nucleic acids (PNA)) that generally comprise a nucleic acid sequence complementary to a contiguous nucleic acid sequence in a miR gene product. The antisense nucleic acid can comprise a nucleic acid sequence that is 50-100% complementary, 75-100% complementary, or 95-100% complementary to a contiguous nucleic acid sequence in a miR gene product. Nucleic acid sequences of particular human miR gene products are provided in the Tables herein. Without wishing to be bound by any theory, it is believed that the antisense nucleic acids activate RNase H or another cellular nuclease that digests the miR gene product/antisense nucleic acid duplex.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators, such as acridine, or one or more nuclease-resistant groups.

Antisense nucleic acids can be produced chemically or biologically, or can be expressed from a recombinant plasmid or viral vector, as described above for the isolated miR gene products. Exemplary methods for producing and testing are within the skill in the art; see, e.g., Stein and Cheng (1993), Science 261:1004 and U.S. Pat. No. 5,849,902 to Woolf et al., the entire disclosures of which are incorporated herein by reference.

Expression of a given miR gene can also be inhibited by an enzymatic nucleic acid. As used herein, an "enzymatic nucleic acid" refers to a nucleic acid comprising a substrate binding region that has complementarity to a contiguous nucleic acid sequence of a miR gene product, and which is able to specifically cleave the miR gene product. The enzymatic nucleic acid substrate binding region can be, for example, 50-100% complementary, 75-100% complementary, or 95-100% complementary to a contiguous nucleic acid sequence in a miR gene product. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described above for the isolated miR gene products. Exemplary methods for producing and testing dsRNA or siRNA molecules are described in Werner and Uhlenbeck (1995), Nucl. Acids Res. 23:2092-96; Hammann et al. (1999), Antisense and Nucleic Acid Drug Dev. 9:25-31; and U.S. Pat. No. 4,987,071 to Cech et al, the entire disclosures of which are incorporated herein by reference.

Administration of at least one miR gene product, or at least one compound for inhibiting miR expression, will inhibit the proliferation of cancer cells in a subject who has a cancer (e.g., AML). As used herein, to "inhibit the proliferation of a cancer cell" means to kill the cell, or permanently or temporarily arrest or slow the growth of the cell. Inhibition of cancer cell proliferation can be inferred if the number of such cells in the subject remains constant or decreases after administration of the miR gene products or miR gene expression-inhibiting compounds. An inhibition of cancer cell proliferation can also be inferred if the absolute number of such cells increases, but the rate of tumor growth decreases.

The number of cancer cells in the body of a subject can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The miR gene products or miR gene expression-inhibiting compounds can be administered to a subject by any means suitable for delivering these compounds to cancer cells of the subject. For example, the miR gene products or miR expression-inhibiting compounds can be administered by methods suitable to transfect cells of the subject with these compounds, or with nucleic acids comprising sequences encoding these compounds. In one embodiment, the cells are transfected with a plasmid or viral vector comprising sequences encoding at least one miR gene product or miR gene expression-inhibiting compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor-mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy) propyl]-N,N,N-trimethyl-ammonium methylsulfate, Boehringer-Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

A miR gene product or miR gene expression-inhibiting compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and direct injection into the tumor.

In the present methods, a miR gene product or miR gene product expression-inhibiting compound can be administered to the subject either as naked RNA, in combination with a delivery reagent, or as a nucleic acid (e.g., a recombinant plasmid or viral vector) comprising sequences that express the miR gene product or miR gene expression-inhibiting compound. Suitable delivery reagents include, e.g., the Mirus Transit TKO lipophilic reagent; LIPOFECTIN; lipofectamine; cellfectin; polycations (e.g., polylysine) and liposomes.

Recombinant plasmids and viral vectors comprising sequences that express the miR gene products or miR gene expression-inhibiting compounds, and techniques for delivering such plasmids and vectors to cancer cells, are discussed herein and/or are well known in the art.

In a particular embodiment, liposomes are used to deliver a miR gene product or miR gene expression-inhibiting compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, for example, as described in Szoka et al. (1980), Ann. Rev. Biophys. Bioeng. 9:467; and U.S. Pat. Nos. 4,235,871, 4,501,728, 4,837,028, and 5,019,369, the entire disclosures of which are incorporated herein by reference.

The liposomes for use in the present methods can comprise a ligand molecule that targets the liposome to cancer cells. Ligands that bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both an opsonization-inhibition moiety and a ligand.

Opsonization-inhibiting moieties for use in preparing the liposomes of the invention are typically large hydrophilic polymers that are bound to the liposome membrane. As used herein, an opsonization-inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is incorporated herein by reference.

Opsonization-inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) or derivatives thereof; e.g., methoxy PEG or PPG, and PEG or PPG stearate; synthetic polymers, such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization-inhibiting polymer can be a block copolymer of PEG and either a polyamino acid, polysaccharide, polyamidoamine, polyethyleneamine, or polynucleotide. The opsonization-inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or a derivative thereof. Liposomes modified with PEG or PEG-derivatives are sometimes called "PEGylated liposomes."

The opsonization-inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using Na(CN)BH$_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example, solid tumors (e.g., AML cancers), will efficiently accumulate these liposomes; see Gabizon, et al. (1988), Proc. Natl. Acad. Sci., U.S.A., 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR gene products or miR gene expression-inhibition compounds (or nucleic acids comprising sequences encoding them) to tumor cells.

The miR gene products or miR gene expression-inhibition compounds can be formulated as pharmaceutical compositions, sometimes called "medicaments," prior to administering them to a subject, according to techniques known in the art. Accordingly, the invention encompasses pharmaceutical compositions for treating AML cancer. In one embodiment, the pharmaceutical composition comprises at least one isolated miR gene product, or an isolated variant or biologically-active fragment thereof, and a pharmaceutically-acceptable carrier. In a particular embodiment, the at least one miR gene product corresponds to a miR gene product that has a decreased level of expression in AML cancer cells relative to suitable control cells.

In other embodiments, the pharmaceutical compositions of the invention comprise at least one miR expression-inhibition compound. In a particular embodiment, the at least one miR gene expression-inhibition compound is specific for a miR gene whose expression is greater in AML cancer cells than control cells.

Pharmaceutical compositions of the present invention are characterized as being at least sterile and pyrogen-free. As used herein, "pharmaceutical compositions" include formulations for human and veterinary use. Methods for preparing pharmaceutical compositions of the invention are within the skill in the art, for example, as described in Remington's Pharmaceutical Science, 17th ed., Mack Publishing Company, Easton, Pa. (1985), the entire disclosure of which is incorporated herein by reference.

The present pharmaceutical compositions comprise at least one miR gene product or miR gene expression-inhibition compound (or at least one nucleic acid comprising a sequence encoding the miR gene product or miR gene expression-inhibition compound) (e.g., 0.1 to 90% by weight), or a physiologically-acceptable salt thereof, mixed with a pharmaceutically-acceptable carrier. In certain embodiments, the pharmaceutical composition of the invention additionally comprises one or more anti-cancer agents (e.g., chemotherapeutic agents). The pharmaceutical formulations of the invention can also comprise at least one miR gene product or miR gene expression-inhibition compound (or at least one nucleic acid comprising a sequence encoding the miR gene product or miR gene expression-inhibition compound), which are encapsulated by liposomes and a pharmaceutically-acceptable carrier. In one embodiment, the pharmaceutical composition comprises a miR gene or gene product that is not miR-15, miR-16, miR-143 and/or miR-145.

Especially suitable pharmaceutically-acceptable carriers are water, buffered water, normal saline, 0.4% saline, 0.3% glycine, hyaluronic acid and the like.

In a particular embodiment, the pharmaceutical compositions of the invention comprise at least one miR gene product or miR gene expression-inhibition compound (or at least one nucleic acid comprising a sequence encoding the miR gene product or miR gene expression-inhibition compound) that is resistant to degradation by nucleases. One skilled in the art can readily synthesize nucleic acids that are nuclease resistant, for example by incorporating one or more ribonucleotides that is modified at the 2'-position into the miR gene product. Suitable 2'-modified ribonucleotides include those modified at the 2'-position with fluoro, amino, alkyl, alkoxy and O-allyl.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one miR gene product or miR gene expression-inhibition compound (or at least one nucleic acid comprising sequences encoding them). A pharmaceutical composition for aerosol (inhalational) administration can comprise 0.01-20% by weight, preferably 1%-10% by weight, of the at least one miR gene product or miR gene expression-inhibition compound (or at least one nucleic acid comprising a sequence encoding the miR gene product or miR gene expression-inhibition compound) encapsulated in a liposome as described above, and a propellant. A carrier can also be included as desired; e.g., lecithin for intranasal delivery.

The pharmaceutical compositions of the invention can further comprise one or more anti-cancer agents. In a particular embodiment, the compositions comprise at least one miR gene product or miR gene expression-inhibition compound (or at least one nucleic acid comprising a sequence encoding the miR gene product or miR gene expression-inhibition compound) and at least one chemotherapeutic agent. Chemotherapeutic agents that are suitable for the methods of the invention include, but are not limited to, DNA-alkylating agents, anti-tumor antibiotic agents, anti-metabolic agents, tubulin stabilizing agents, tubulin destabilizing agents, hormone antagonist agents, topoisomerase inhibitors, protein kinase inhibitors, HMG-CoA inhibitors, CDK inhibitors, cyclin inhibitors, caspase inhibitors, metalloproteinase inhibitors, antisense nucleic acids, triple-helix DNAs, nucleic acids aptamers, and molecularly-modified viral, bacterial and exotoxic agents. Examples of suitable agents for the compositions of the present invention include, but are not limited to, cytidine arabinoside, methotrexate, vincristine, etoposide (VP-16), doxorubicin (adriamycin), cisplatin (CDDP), dexamethasone, arglabin, cyclophosphamide, sarcolysin, methylnitrosourea, fluorouracil, 5-fluorouracil (5FU), vinblastine, camptothecin, actinomycin-D, mitomycin C, hydrogen peroxide, oxaliplatin, irinotecan, topotecan, leucovorin, carmustine, streptozocin, CPT-11, taxol, tamoxifen, dacarbazine, rituximab, daunorubicin, 1-β-D-arabinofuranosylcytosine, imatinib, fludarabine, docetaxel and FOLFOX4.

The invention also encompasses methods of identifying an anti-AML cancer agent, comprising providing a test agent to a cell and measuring the level of at least one miR gene product in the cell. In one embodiment, the method comprises providing a test agent to a cell and measuring the level of at least one miR gene product associated with decreased expression levels in AML cancer cells. An increase in the level of the miR gene product in the cell, relative to a suitable control (e.g., the level of the miR gene product in a control cell), is indicative of the test agent being an anti-AML cancer agent.

In a particular embodiment, the at least one miR gene product associated with decreased expression levels in AML cancer cells is selected from the group consisting of the miR-NAs as shown in any one of FIGS. 5-6, 8-18 and 21 (Tables 1-2, 5-15 and 18) and a combination thereof.

In other embodiments the method comprises providing a test agent to a cell and measuring the level of at least one miR gene product associated with increased expression levels in AML cancer cells. A decrease in the level of the miR gene product in the cell, relative to a suitable control (e.g., the level of the miR gene product in a control cell), is indicative of the test agent being an anti-AML cancer agent.

In a particular embodiment, at least one miR gene product associated with increased expression levels in AML cancer cells is selected from the group consisting of miR-20, miR-25, miR-191, miR-199a, and miR-199b and a combination thereof.

Suitable agents include, but are not limited to drugs (e.g., small molecules, peptides), and biological macromolecules (e.g., proteins, nucleic acids). The agent can be produced recombinantly, synthetically, or it may be isolated (i.e., purified) from a natural source. Various methods for providing such agents to a cell (e.g., transfection) are well known in the art, and several of such methods are described hereinabove. Methods for detecting the expression of at least one miR gene product (e.g., Northern blotting, in situ hybridization, RT-PCR, expression profiling) are also well known in the art. Several of these methods are also described herein.

The invention will now be illustrated by the following non-limiting examples.

Exemplification

Methods

Patients and cell samples. Leukemic samples from 158 patients with newly diagnosed AML and 54 samples from patients with AML at relapse (34) or with refractory disease (20) were obtained from the Cell and Tissue Bank at MD Anderson Cancer Center (n=202) and Thomas Jefferson University (n=10), after informed consent was signed according to institutional guidelines (FIG. 4 (Table 1)).

Bone marrow or peripheral blood samples were collected, prepared by Ficoll-Hypaque (Nygaard) gradient centrifugation and cryopreserved. Cytogenetic analyses of the samples were performed at presentation, as previously described[16]. The criteria used to describe a cytogenetic clone and karyotype followed the recommendations of the International System for Human Cytogenetic Nomenclature[17]. An independent set of 36 patients with AML was used to validate miRNAs within the microarray signatures by using qRT-PCR (FIG. 4 (Table 1)). Complete remission (CR) was defined by the presence of <than 5% of blasts in the bone marrow aspirate, absolute peripheral neutrophil count $>1 \times 10^9$/l and platelets $>100 \times 10^9$/l.

Peripheral blood mature granulocytes and monocytes, bone marrow CD71+ selected erythrocytes precursors and CD34+ cells from 4 healthy donors, except for CD34+(10 donors) were purchased from Allcells. In vitro differentiated megakaryocytes were obtained as previously described[18].

RNA Extraction and MiRNA Micro Array Experiments.

RNA extraction and miRNA microchip experiments were performed as described in detail elsewhere[19]. Briefly, 5 ug of total RNA from 176 AML patients were hybridized in quadruplicate with probes corresponding to 250 human mature and precursor miRNAs (as described in the miRBase on November 2005)[20].

Real-Time Quantification of MicroRNAs.

The single tube TaqMan miRNAs as previously described[21] using PCR 9700 Thermocycler ABI Prism 7900HT and the sequence detection system (Applied Biosystems) was selected because it had the least expression variability in the microarray patient data set. Comparative real-time PCR was performed in triplicate, including no-template controls. Relative expression was calculated using the comparative $C_t$ method Data Analysis.

Microarray images were analyzed using GENEPIX PRO. Average values of the replicate spots of each miRNA were background subtracted, log 2 transformed, normalized and retained in the expression table when measured as present in at least 10% of the samples. Normalization was performed over a set of housekeeping genes (FIG. 7 (Table 4)) printed onto the chip interspersed through the miRNA probes. In two class comparisons (i.e., CD34 vs. AML) differentially expressed miRNAs were identified by using the test procedure within the Significance Analysis of Microarrays (SAM)[22]. SAM calculates a score for each gene on the basis of the change of expression relative to the standard deviation of all measurements. Since this is a multiple test, permutations are performed to calculate the false discovery rate (FDR) or q-value. mRNAs with FDRs less than 5% and fold changes more than 2 were considered for further analysis. All data were submitted to the Array Express database with the use of MIAMExpress (accession numbers pending).

Statistical Analysis.

Fisher's exact test, t-Test and chi-square were used to compare baseline characteristics and average miRNA expression between groups of patients. All reported P values were two-sided and obtained using the SPSS software package (SPSS 10.0). Overall survival was calculated from the time of diagnosis until the date of last follow up and e vent-free survival (EFS) from the time of diagnosis until relapse or death. Data were censored for patients who were alive at the time of last follow up. To perform the survival and generate a Kaplan-Meier (KM) plot, miRNA levels measured on the chips and by qRT-PCR were converted into discrete variables by splitting the samples in two classes (high and low expression, according to the median expression in the full set of samples). Survival curves were obtained for each group and compared by using the log-rank test. Hazard Ratios with their 95% confident intervals obtained from the KM method are also reported.

Target Prediction and Microarray Validation.

Data validation. To validate the microarray data we used Pearson correlation and linear regression analysis (SPSS software) using 42 miRNA measurements in 10 patients. These functions examine each pair of measurements (one from the chip and the other from RT-PCR) to determine whether the two variables tend to move together, that is whether the large r values from the chip (high expression) are associated with the lower values from the qRT-PCR (delta Ct). A negative correlation is expected because the qRT-PCR values (delta Ct) are inversed to the expression levels of miRNAs. Log values for both chip and qRT-PCR miRNA measurements were used.

Target prediction. MicroRNA targets were predicted in silico by using TARGETSCAN[32] and PICTAR[33]; both databases predict conserved 3'UTR miRNA targets.

Results.

AML patients reveal a distinct spectrum of miRNA expression with respect to normal CD34+ progenitor cells.

Figure 1A:
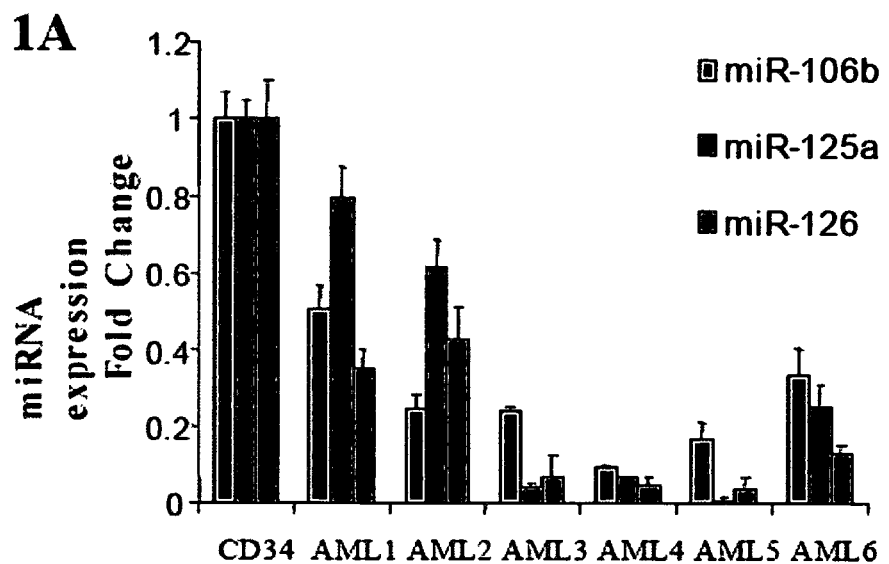
FIGS. 1A-F. Validation of microarray data by quantification of mature miRNAs by qRT-PCR.
Figure 1B:
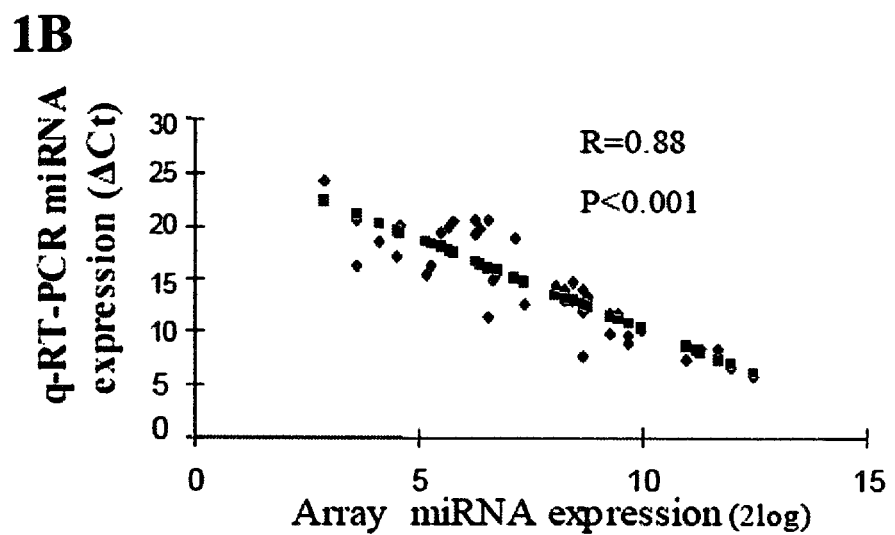

As a first step to wards understanding the possible involvement of miRNAs in the pathogenesis of AML, we analyzed the miRNA expression in 122 newly diagnosed AML patient samples and CD34+ cells from 10 different donors using a miRNA microarray platform[19] (Clinical data in FIG. 4 (Table 1)). SAM identified only down-regulated miRNAs in AML samples compared with CD34+ cells (Table S 2, supporting information). We confirmed many of these differentially expressed miRNAs by using qRT-PCR (FIG. 1A). Additionally, to validate the microarray platform we performed qRT-PCR for miRNAs that were highly, intermediate and low expressed on the chip. As shown in FIG. 1B the miRNA levels measured by either the microarray or the qRT-PCR were very concordant and there was a highly significant correlation between the measures in the two platforms (r=0.88, p<0.001).

Figure 1C:
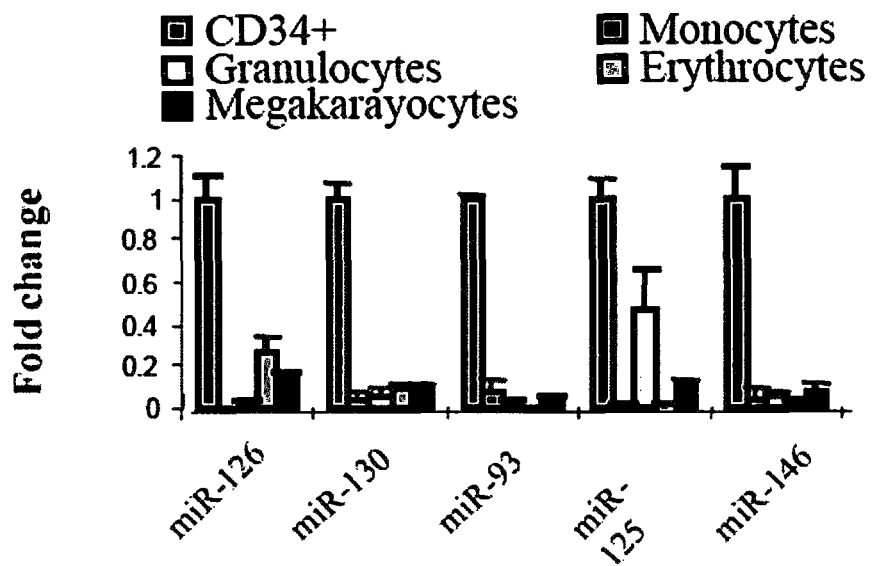
Figure 1D:
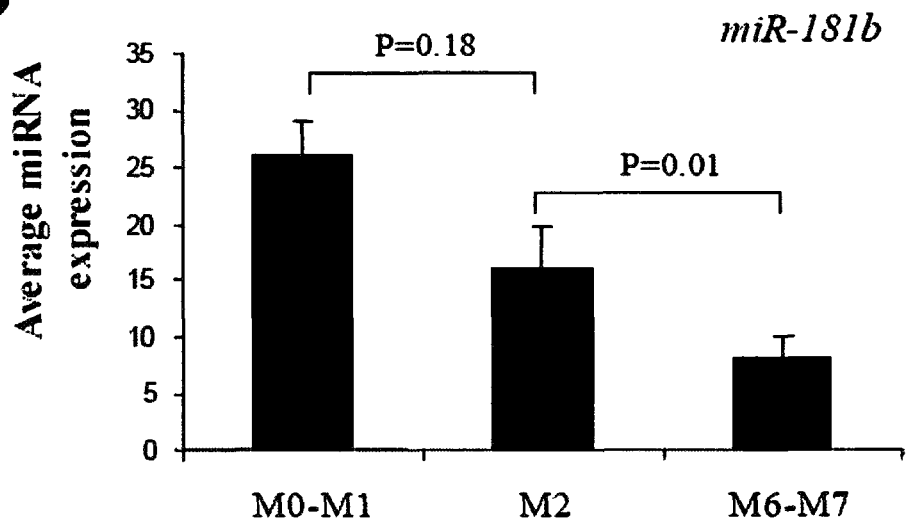

A miRNA signature correlates with hematopoietic differentiation and FAB classification.

mRNA expression has been shown to be informative of the hematopoietic developmental lineage and differentiation stage of tumors[11]. As different profiles characterize normal vs. malignant cells in AML patients, we determine d by qRT-PCR the expression pattern of the most differentially expressed miRNAs between AML samples and CD34+ cells among a panel of human hematopoietic cells, including mature granulocyte s and monocyte s, as well as erythrocyte and megakaryocyte precursors. Many miRNAs down-regulated in AML were also down-regulated in mature and precursor hematopoietic cells (FIGS. 1C and 3A). Two recent studies have described widespread miRNA down-regulation during in vitro differentiation of CD34+ cells to several lineages[18,23]. These results suggest that a subset of miRNAs in leukemia follow closely the differentiation patterns of miRNA expression in normal hematopoiesis. If miRNAs reflect the stage of cell differentiation in leukemia patients, they should also correlate with the French-American and British (FAB) classification of AML[24], which is based on cytomorphology and immunophenotype, both closely associated with the differentiation stage of the leukemia. Indeed, we identified signatures associated with FAB classification. (FIGS. 9-12, Tables 6-9). Within the FAB M 0-M1 signature, we identified several miR-181 family members, as well as other miRNAs highly expressed in CD34+ cells, suggesting an expression profile closer to that of stem cells (FIG. 9 (Table 6)). The expression of miR-181b is in fact down-regulated in mature and committed precursors hematopoietic cells from all lineages (FIG. 3A) and similar results were observed in the most differentiated leukemias like FAB M6-M7 (FIG. 1D).

mRNAs Positively Correlated with White Blood Cell and Blasts Counts

We then investigated whether miRNAs are associated with pretreatment patient characteristics such as age, sex, white blood cell (WBC) count, bone marrow or peripheral blood blasts percentage. We detected a positive correlation in several miRNAs, including miR-155, miR-30b, miR-30c, miR-25 and miR-181b with WBC count, peripheral blood and marrow blast percentage (FIG. 13 (Table 10)).

MicroRNA Signatures Associated with Defined Cytogenetic Subgroups.

To identify miRNA s associated with known cytogenetic abnormalities in AML we studied 116 AML samples with at least 20 metaphases analyzed by conventional karyotype by using permutation adjusted t-tests within SAM. These data are summarized in FIG. 5 (Table 2).

AML with Normal Karyotype.

Figure 1E:
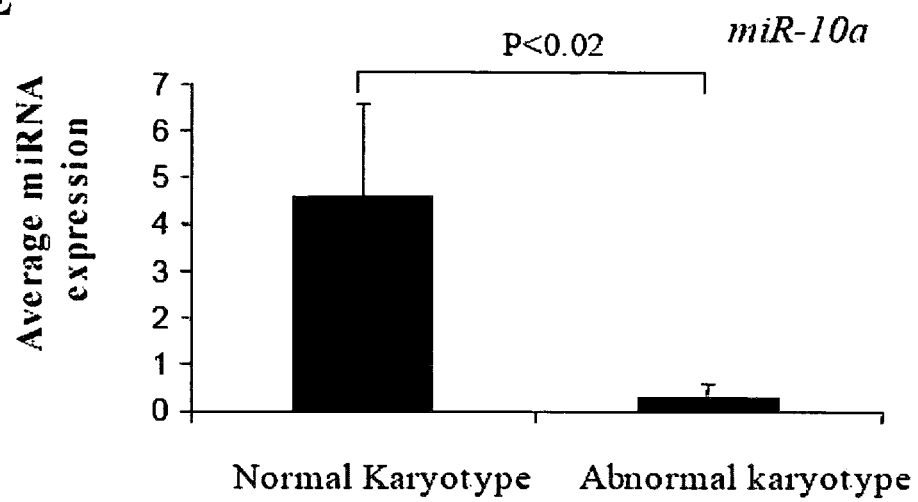

We identified a signature distinguishing AML cases with a normal karyotype from all other cases of AML with abnormal karyotype (FIG. 14 (Table 11), FIG. 3B). Among the up-regulated genes, miR are located within the cluster of HOX genes, which have been shown to be over expressed in AML with a normal karyotype 6 (FIG. 1E, FIG. 5 (Table 2)). In particular, we and others have shown that Hox embedded miRNAs like miR-10a and miR-196b target several Hox genes, revealing a complex layer of regulation for this family of transcription factors[18,25].

Two previous studies identified high levels of expression of the DNA methyl transferase genes DNMT3A and 3B in normal karyotype AML samples suggesting a potential role for abnormal methylation in the pathogenesis of this subtype[5-6]. Intriguingly, among the down-regulated miRNAs in the normal karyotype group, are present two miRNAs (miR-200c and miR-182), predicted to target DNMT3A and miR-, which is proposed to target DNMT3B. Thus, the down-regulation of these miRNAs may contribute to the over expression of both DNMT3 genes in normal karyotype AML cells.

11q23 Abnormalities

Figure 1F:
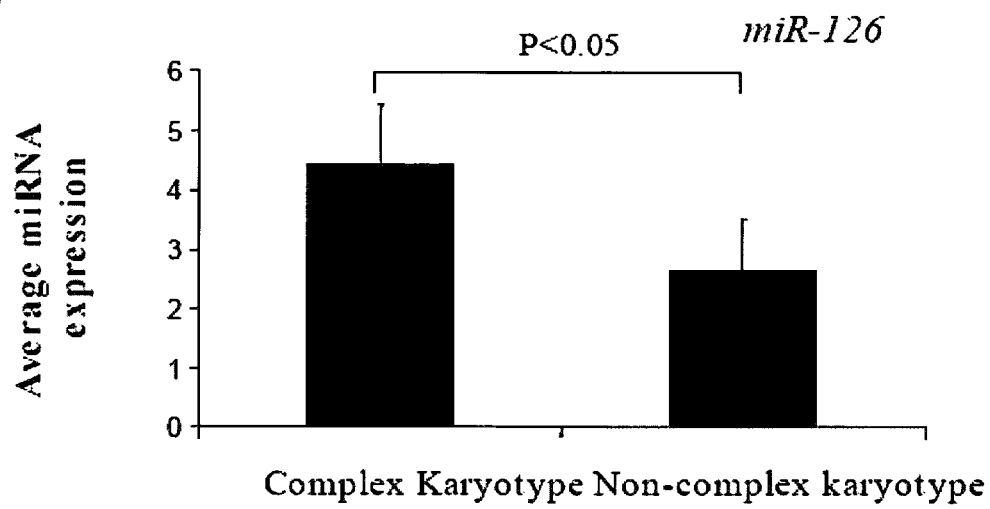

Among the genes down-regulated in patients with t(9;11) [5] and t(6;11)[4] (FIG. 15 (Table 12)), many are predicted to target Hox genes which have been described over-expressed and associated with poor prognosis in this group of patients, i.e., HOXA9 (let7f), HOSA10 (iR-15a), PBX3(let07f, miR-15a and miR-196b) and MEISI (miR-331)[6] (FIG. 15 (Table 12)). Likewise, members of the miR-29 family, also down-regulated in this group, are predicted to target the anti-apoptotic MCLI gene Complex Karyotype Samples with 3 or more cytogenetics abnormalities share a common signature that includes miR-126, miR-26a, miR-34b, miR-30c and miR-301 as the most discriminative genes for this group. (FIG. 16 (Table 13)). Likewise in patients with isolated loss of the chromosome 7, miR-126 was up-regulated (Table S11). Interestingly this miRNA is highly expressed in CD34+ stem cells and down-regulated in other AMLs, except in those with complex karyotype. These results were confirmed in an independent set of AML patients with complex (N=6) and non-complex cytogenetic abnormalities (N=22) by using qRT-PCR (FIG. 1F).

Trisomy 8

The signature obtained using SAM identified many up-regulated miRNAs in patient samples with isolated trisomy 8 (FIG. 18 (Table 15)). Among the up-regulated miRNAs, miR124a and miR-30d are located at 8p21 and 8q23 respectively, suggesting that a gene dosage effect may play a role in the up-regulation of these miRNAs.

Micrornas Expression in Relapsed AML Patients

We further investigated miRNAs expression profiles of 54 patients with relapsed acute myeloid leukemia by using our miRNA platform (FIG. 19 (Table 16)). We did not find strong differences between new and treated patients, as reflected by non-significant statistical scores and fold change s lower than 2 (data not shown). However, we observed in these patients FAB and cytogenetics signatures highly similar to those of the new patients (FIGS. 8-17; Tables 5-14), thus confirming the previously described findings. These data suggest that miRNAs expression is largely driven by the differentiation stage of the leukemia and cytogenetics.

MicroRNAs Associated with the Outcome

We identified a small number of miRNAs with a false discovery rate lower than 1% and a SAM survival score (Cox regression) higher than 2 associated with overall survival in 122 newly diagnosed AML patients. All the identified genes: miR-17-5p, MIR-20, miR-miR-182, miR-191, miR-199a and miR-199b when over-expressed, adversely affected overall survival (FIG. 6 (Table 3)). We then estimated the survival probabilities of the 122 AML patients with high or low expression of the above miRNAs by using Kaplan-Meier method and log-rank test for survival curves comparisons. We confirmed the SAM results for miR-20 (FIG. 2A), miR-25 (FIG. 2B), miR-191, miR-199a and miR-199b, except for miR-17-5p and miR-182 (p=0.06) [Data not shown]. To assess whether and by using qRT-PCR in an independent sample of 36 patients with AML, we measured miR-20 and miR-25 by using qRT-PCR in an independent sample of 36 patients with AML.

Patients with high expression of miR-20 or miR-25 were found to have significant shorter overall survival (OS) (FIGS. 2A and 2B) and event-free survival (miR-20 p=0.012, HR=2.39 CI 95%:1.3-5.2 and miR-25 p=0.018, HR=2.23 CI 95%:1.7-4.9) than AML patients with low expression. None of the other clinical characteristics, including sex, age, unfavorable cytogenetics, white blood cells and peripheral blasts counts were significantly associated with survival in this independent set of 36 AML patients (data not shown).

mRNAs Associated with Failure to Achieve Remission with Induction Treatment

As we had shown that biological and genetic findings in AML patients correlated with expression of different miRNAs, we then further investigated the relation between treatment response and miRNA expression. To identify miRNAs associated with induction treatment response, we analyzed the expression of miRNAs in a group of 24 AML patients at diagnosis, all treated with idarubicin 12 mg/m 2 daily on days 1 to 3 and cytarabine 1500 mg/m 2 continuous infusion for 4 days (FIG. 20 (Table 17)). SAM identified 25 miRNAs down-regulated at diagnosis in patients who had treatment failure (FIG. 21 (Table 18)). Among them, miR-29b and miR-29c are predicted to target MCLI, a gene associated with resistance to a variety of chemotherapeutic agents[26]. To confirm these results, we measured miR-29b by qRT-PCR in an independent set of AML patients with similar baseline characteristics but treated with various chemotherapy protocols. We found that miR-29b is down-regulated in patients with treatment induction failure compared with patients who achieve complete remission (FIG. 3C).

Discussion

In this study we used a microarray platform to perform genome wide miRNome analysis of AML samples and their progenitor CD34+ cells. Despite the fact that some miRNAs were up-regulated in AML patients compared with CD34+ cells, most of the miRNAs were down-regulated. Some of the down-regulated miRNAs include markers for the differentiation stage of the leukemia that correlate well with the FAB classification of AML. Lu et al. reported that miRNAs reflect the developmental lineage and differentiation state of tumors[11]. Whether the miRNA subsets identified here are only markers for the differentiation stage or some of these miRNAs have a pathogenic role remains to be elucidated.

Using SAM, we identified molecular signatures associated with several cytogenetic group s. Among the strongest signatures were those associated to 11q23 rearrangements, normal karyotype and trisomy 8.

A subset of miRNAs acts as oncogenic miRNAs.

The up-regulated cluster spanning miR-17 and miR-20, target E2FI[27], thus impacting over the cell cycle regulation. In contrast, members of the miR-29 family, down-modulated in AML and associated with failure to achieve remission, is predicted to target MCLI, a critical apoptosis regulator, found up-regulated in cells that are resistant to a variety of chemotherapeutic agents[26]. Moreover other members of this family have been identified in the signature associated with short event-free survival in CLL patients 28 and in AML cancer 29, indicating that this miRNA could be a tumor suppressor non-coding gene.

We describe molecular signatures associated with overall and event-free survival (OS). Several observations strengthen our results. First, we identified miRNAs associated with survival despite the overall poor prognosis and short survival of the patients studied where outcome differences would be difficult to demonstrate. Second, two of the miRNAs associated with survival (miR-20 and miR-25) were also correlated with high WBC and blast counts, all features closely relate d with survival. Third, we identified several up-regulated miRNAs in common with the shared signatures of six solid cancers (such as miR-17, miR-20 and miR-191)[10] some of them (like miR-17 and miR-20) with well characterized roles in oncogenesis[27-30].

In summary, we demonstrate s that a subset of miRNAs are markers for the differentiation stage of the leukemia and correlate with the FAB classification, while others are clearly deregulated in AML, associate d with cytogenetic groups and outcome. Finally, we show that miRNAs may be involved in leukemogenesis acting as oncogenes and tumor suppressors.

The foregoing embodiments and advantages are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

All scientific and patent publications referenced herein are hereby incorporated by reference. The invention having now been described by way of written description and example, those of skill in the art will recognize that the invention can be practiced in a variety of embodiments, that the foregoing description and example is for purposes of illustration and not limitation of the following claims.

The relevant teachings of all publications cited herein that have not explicitly been incorporated by reference, are incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

REFERENCES

1. Lowenberg B, Downing J. R., Burnett A. Acute Myeloid leukemia. N Engl J Med 1999; 341: 1051-1062.

2. Grimwade D, Haferlach T. Gene expression profiling in acute myeloid leukemia. N Engl J Med 2004; 350:1676-7.
3. Burnett A K. Current controversies: which patients with acute myeloid leukemia should receive bone marrow transplantation? An adult theater's view. Br. J. Haematol 2002; 118:357-64.
4. Drobyski W R. The role of allogeneic transplantation in high-risk acute myeloid leukemia. Leukemia 2004; 10:1565-8.
5. Bullinger L, Dohner K, Bair E, et al. Use of gene-expression profiling to identify prognostic subclasses in adult acute myeloid leukemia. N Eng J Med 2004; 350:1605-1 61 6.
6. Valk P J M, Verhaak G W, Beijen M A. Prognostically useful gene-expression profiles in acute myeloid leukemia. N Eng J Med 2004; 350: 1617-1628.
7. Pasquinelli A E, Hunter S, Bracht J. MicroRNAs: a developing story. Curr O, Genet Dev 2005; 15: 200-5.
8. Bartel D. MicroRNAs: genomics, Biogenesis, Mechanism, and Function. Cell 2004; 116:281-297.
9. Chen C Z, Li L, Lodish H, Bartel D. MicroRNAs Modulate Hematopoietic lineage Differentiation. Science 2004; 303: 83-86.
10. Volinia S, Calin G, Liu C G, et al. A microRNA expression signature in human solid tumors defines cancer targets. Proc Nad Acad Sci USA 2006; 103: 2257-61.
11. Lu J, Getz G, Miska E A, et al. MicroRNA expression profiles classify human cancers. Nature 2005; Jun. 9; 435: 834-8.
12. Calin G A, Liu C G, Sevignani C, et al. MicroRNA profiling reveals distinct signatures in B-Cell Chronic Lymphocytic leukemias. Proc Nad Acad Sci USA 2004; 101: 11755-60.
13. Eis P S, Tam W, Sun, L. Accumulation of miR-155 and BIC RNA in human B cell lymphomas. Proc Nad Acad Sci USA 2005; 102: 3627-32.
14. Metzler M, Wilda M, Busch K, et al. High expression of miR-155/BIC RNA in children with Burkitt lymphoma. Genes Chromosomes and Cancer 2004; 39:167-9.
15. Costinean, S. et al. Pre B cell proliferation and lymphoblastic leukemia/high grade lymphoma in Eµ miR155 transgenic mice. Proc Nad Acad Sci USA 2006; 103: 7024-9.
16. Bloomfield C D. Prognostic factors for selecting curative therapy for adult acute myeloid leukemia. Leukemia 1992; 6:65-67. 21.
17. An International System for Human Cytogenetic Nomenclature (1985) ISCN 1985. Report of the Standing Committee on Human Cytogenetic Nomenclature. Bi Orig Artic Ser 1985; 21:1-117.
18. Garzon R, Pichiorri F, Palumbo T, et al. MicroRNAs fingerprints during human megakaryocytopoiesis. Proc Nad Acad Sci USA 2006; 103: 5078-83.
19. Liu C G, Calin G A, Meloon B, et al. An oligonucleotide microchip for genomic-wide microRNA profiling in human and mouse tissues. Proc Nad Acad Sci USA 2004; 101: 11755-60.
20. Griffiths-Jones S. The microRNA registry. Nucleic Acids Res 2004; 32, Database issue D109-D111.
21. Chen C, Ridzon D A, Broomer A J, et al. Real-Time quantification of microRNAs by stem-loop RT-PCR. Nucleic Acids Res 2005:33:e179.
22. Tusher V G, Tibshirani R, Chu G. Significant analysis of microarrays applied to the ionizing radiation response. Proc Natl Acad Sci USA 2001; 98:5116:21.
23. Felli N, Pelosi E, Beta R, et al. Lineage-Specific Expression and functional Relevance of MicroRNA genes in Normal Hematopoiesis. Blood (ASH national meetings abstract) 2006; 106: 2263.
24. French-American-British (FAB) Cooperative Group. Proposed revised criteria for the classification of acute myeloid leukemia. Ann Intern Med. 1985; 103:620-685.
25. Yekta S, Shih I H, Bartel D P. Micro-RNA direct cleavage of HOXB8 mRNA. Science 2004; 304:594-6.
26. Zhou P, Qian L, Kozopas K M, Craig R W: Mcl-1, a Bcl-2 family member, delays the death of hematopoietic cells under a variety of apoptosis-inducing conditions. Blood 1997; 89:630.
27. O'Donnell K A, Wentzel E A, Zeller K I, Dang C V, Mendell J T. C-myc regulated microRNAs modulate E2F1 expression. Nature 2005; 435:839-43.
28. Calin G A, Terracing M, Camino A, et al. A MicroRNA signature associated with prognosis and progression in chronic lymphocytic leukemia. N Engl J Med. 2005; 353: 1793-801.
29. Yanaihara N, Caplen N, Bowman, E, et al. Unique microRNA molecular profiles in AML cancer diagnosis and prognosis. Cancer Cell 2006; 9:189-98.
30. He L, Thomson J M, Hemann M T. A microRNA polycistron as a potential oncogene. re 2005; 435: 828-33.
31. Lewis B P, Shih I H, Jones-Rhoades M W, Bartel P, Burge C B. Prediction of mammalian microRNA targets. Cell 2003; 115:787-798.32. Krek A, Grün D, Poy M, et al. Combinatorial microRNA target Nature G 37: 495-500.
32. Lewis B P, Burge C B, Bartel D. Conserved seed pairing often flanked by adenosines, indicates that thousands of human genes are microRNA targets. Cell 2005; 120:15-20.
33. Krek A, Grun D, Poy M N, et al. Combinatorial microRNA target predictions. Nat. Genet. 2005; 37: 495-500.

What is claimed is:

1. A method of predicting chemotherapy treatment failure risk in a subject with acute myeloid leukemia (AML), comprising:
    a) obtaining a test sample from subject having, or suspected of having AML, wherein the sample is extracted from at least one of: blood, bone marrow, and tissue suspected of having leukemic cells,
    b) measuring the level of miR-29 gene product in the test sample by conducting laboratory analysis of the sample so as to obtain physical data regarding the expression level of miR-29 gene product in the sample,
    c) comparing the level of miR-29 gene product in the test sample relative to a control level of miR-29 gene product, and
    d) predicting the subject's chemotherapy treatment failure risk,
    wherein, if the level of miR-29 gene product in the test sample is low relative to the control level of miR-29 gene product, the subject is predicted to have a high chemotherapy treatment failure risk.

2. A method of claim 1, wherein the miR-29 gene product is miR-29b gene product.

3. A method of claim 1, wherein the miR-29 gene product is miR-29c gene product.

4. A method of claim 1, wherein the chemotherapy is idarubicin.

5. A method of claim 1, wherein the chemotherapy is cytarabine.

6. The method of claim 1 wherein the measuring of the at least miR-29 gene product in the test sample is carried out by analyzing the test sample with a microarray and/or Northern blot electrophoretic device.

7. A method of diagnosing whether a subject with AML has chemotherapy treatment induction failure, comprising:
   a) obtaining a test sample from subject having AML, wherein the sample is extracted from at least one of: blood, bone marrow, and tissue suspected of having leukemic cells,
   b) measuring the level of miR-29 gene product in a test sample from a subject with AML by conducting laboratory analysis of the sample so as to obtain physical data regarding the expression level of miR-29 gene product in the sample,
   c) comparing the level of miR-29 gene product in the test sample relative to a control level of miR-29 gene product, and
   d) predicting the subject's chemotherapy induction treatment failure,
   wherein, if the level of miR-29 gene product in the test sample is low relative to the control level of miR-29 gene product, the subject is predicted to have a high chemotherapy treatment failure.

8. A method of claim 7, wherein the miR-29 gene product is miR-29b gene product.

9. A method of claim 7, wherein the miR-29 gene product is miR-29c gene product.

10. A method of claim 7, wherein the chemotherapy is idarubicin.

11. A method of claim 7, wherein the chemotherapy is cytarabine.

12. A method of determining the prognosis of a subject with acute myeloid leukemia (AML), comprising: measuring a level of at least one miR-29b gene product in a test sample derived from blood or marrow from the subject, conducting laboratory analysis of the test sample so as to obtain physical data regarding the expression level of at least one miR-29b gene product in the sample, comparing the level of at least one miR-29b gene product in a test sample to a control, and predicting adverse prognosis and chemotherapy treatment induction failure in the subject with AML if a decrease in the level of the miR-29b gene product in the test sample, relative to control levels of miR-29b gene product, is detected.

13. A method of claim 12, wherein the chemotherapy is idarubicin.

14. A method of claim 12, wherein the chemotherapy is cytarabine.

15. A method of determining the prognosis of a subject with acute myeloid leukemia (AML), comprising: measuring a level of at least one miR-29c gene product in a test sample derived from blood or marrow from the subject, conducting laboratory analysis of the test sample so as to obtain physical data regarding the expression level of at least one miR-29c gene product in the sample, comparing the level of at least one miR-29c gene product in a test sample to a control, and predicting adverse prognosis and chemotherapy treatment induction failure in the subject with AML if a decrease in the level of the miR-29c gene product in the test sample, relative to control levels of miR-29c gene product, is detected.

16. A method of diagnosing whether a subject has, or is at risk for developing, acute myeloid leukemia (AML) with an adverse prognosis, comprising:
   (1) reverse transcribing at least one miR-29b RNA from a test sample obtained from the subject's blood or bone marrow to provide a set of target oligodeoxynucleotides;
   (2) hybridizing the target oligodeoxynucleotides to a microarray comprising miR-29b miRNA-specific probe oligonucleotides to provide a hybridization profile for the test sample; and
   (3) comparing the test sample hybridization profile to a hybridization profile generated from a control sample;
   (4) diagnosing the subject as either having, or being at risk for developing, AML with an adverse prognosis if there is a decrease in the signal of at least one miR-29b miRNA compared to control levels of miR-29b gene product.

17. A method of diagnosing whether a subject has, or is at risk for developing, acute myeloid leukemia (AML) with an adverse prognosis, comprising:
   (1) reverse transcribing at least one miR-29c RNA from a test sample obtained from the subject's blood or bone marrow to provide a set of target oligodeoxynucleotides;
   (2) hybridizing the target oligodeoxynucleotides to a microarray comprising miR-29c miRNA-specific probe oligonucleotides to provide a hybridization profile for the test sample; and
   (3) comparing the test sample hybridization profile to a hybridization profile generated from a control sample;
   (4) diagnosing the subject as either having, or being at risk for developing, AML with an adverse prognosis if there is a decrease in the signal of at least one miR-29c miRNA compared to control levels of miR-29c gene product.

* * * * *

UNITED STATES PATENT AND TRADEMARK OFFICE
CERTIFICATE OF CORRECTION

PATENT NO. : 8,530,159 B2
APPLICATION NO. : 13/269404
DATED : September 10, 2013
INVENTOR(S) : Carlo M. Croce It is certified that error appears in the above-identified patent and that said Letters Patent is hereby corrected as shown below:

In the Specification

Column 1, Line 20-23, please update the Statement Regarding Federally Sponsored Research as shown:
This invention was made with government support under grant numbers CA076259, CA016058, and CA081534 awarded by the National Institutes of Health. The government has certain rights in the invention.

Signed and Sealed this
Twenty-first Day of July, 2020

Andrei Iancu
*Director of the United States Patent and Trademark Office*